(12) United States Patent
Warnking

(10) Patent No.: US 12,274,833 B2
(45) Date of Patent: Apr. 15, 2025

(54) METHOD AND APPARATUS FOR TREATMENT OF HYPERTENSION THROUGH PERCUTANEOUS ULTRASOUND RENAL DENERVATION

(71) Applicant: ReCor Medical, Inc., Palo Alto, CA (US)

(72) Inventor: Reinhard J. Warnking, East Setauket, NY (US)

(73) Assignee: ReCor Medical, Inc., Palo Alto, CA (US)

( * ) Notice: Subject to any disclaimer, the term of this patent is extended or adjusted under 35 U.S.C. 154(b) by 433 days.

(21) Appl. No.: 17/451,478

(22) Filed: Oct. 19, 2021

(65) Prior Publication Data

US 2022/0126062 A1 Apr. 28, 2022

Related U.S. Application Data

(63) Continuation of application No. 16/055,014, filed on Aug. 3, 2018, now Pat. No. 11,185,662, which is a
(Continued)

(51) Int. Cl.
*A61M 25/00* (2006.01)
*A61B 17/00* (2006.01)
(Continued)

(52) U.S. Cl.
CPC .... *A61M 25/0082* (2013.01); *A61M 25/1002* (2013.01); *A61N 7/00* (2013.01);
(Continued)

(58) Field of Classification Search
CPC ....................................................... A61B 8/12
See application file for complete search history.

(56) References Cited

U.S. PATENT DOCUMENTS 3,938,502 A 2/1976 Bom
4,554,925 A 11/1985 Young
(Continued)

FOREIGN PATENT DOCUMENTS

DE 20 2005 022 060 11/2012
EP 0623360 11/1994
(Continued)

OTHER PUBLICATIONS

Arruda, M.S., et al. "Development and validation of an ECG algorithm for identifying accessory pathway ablation site in Wolff-Parkinson-White syndrome." J Cardiovasc Electrophysiol, 9:2-12 (1998).
(Continued)

*Primary Examiner* — Joel Lamprecht
*Assistant Examiner* — Nyrobi Celestine
(74) *Attorney, Agent, or Firm* — Theresa Ann Raymer

(57) ABSTRACT

Apparatus and methods for deactivating renal nerves extending along a renal artery of a mammalian subject to treat hypertension and related conditions. An ultrasonic transducer (30) is inserted into the renal artery (10) as, for example, by advancing the distal end of a catheter (18) bearing the transducer into the renal artery. The ultrasonic transducer emits unfocused ultrasound so as to heat tissues throughout a relatively large impact volume (11) as, for example, at least about 0.5 cm$^3$ encompassing the renal artery to a temperature sufficient to inactivate nerve conduction but insufficient to cause rapid ablation or necrosis of the tissues. The treatment can be performed without locating or focusing on individual renal nerves.

22 Claims, 7 Drawing Sheets

Related U.S. Application Data continuation of application No. 13/826,645, filed on Mar. 14, 2013, now Pat. No. 10,039,901, which is a continuation of application No. 13/503,109, filed as application No. PCT/US2010/054637 on Oct. 29, 2010, now Pat. No. 9,981,108.

(60) Provisional application No. 61/292,618, filed on Jan. 6, 2010, provisional application No. 61/256,429, filed on Oct. 30, 2009.

(51) Int. Cl.
*A61B 17/22* (2006.01)
*A61B 18/00* (2006.01)
*A61M 25/10* (2013.01)
*A61N 7/00* (2006.01)
*A61N 7/02* (2006.01)

(52) U.S. Cl.
CPC ........ *A61N 7/022* (2013.01); *A61B 2017/003* (2013.01); *A61B 2017/00323* (2013.01); *A61B 2017/22021* (2013.01); *A61B 2018/00023* (2013.01); *A61M 25/0068* (2013.01); *A61M 2025/1047* (2013.01); *A61M 2025/1068* (2013.01); *A61M 2025/1086* (2013.01); *A61M 2025/1093* (2013.01); *A61N 2007/0026* (2013.01); *A61N 2007/0043* (2013.01)

(56) References Cited

U.S. PATENT DOCUMENTS

| | | |
|---|---|---|
| 4,643,186 A | 2/1987 | Roser |
| 4,650,466 A | 3/1987 | Luther |
| 4,709,698 A | 12/1987 | Johnston et al. |
| 4,802,490 A | 2/1989 | Johnston |
| 4,841,977 A | 6/1989 | Griffith et al. |
| 4,983,169 A | 1/1991 | Furukawa |
| 5,000,185 A | 3/1991 | Yock |
| 5,114,423 A | 5/1992 | Kasprzyk |
| 5,295,992 A | 3/1994 | Cameron |
| 5,295,995 A | 3/1994 | Kleiman |
| 5,308,356 A | 5/1994 | Blackshear et al. |
| 5,324,255 A | 6/1994 | Passafaro et al. |
| 5,327,885 A | 7/1994 | Griffith |
| 5,354,200 A | 10/1994 | Klein et al. |
| 5,354,220 A | 10/1994 | Ganguly et al. |
| 5,368,591 A | 11/1994 | Lennox |
| 5,391,197 A | 2/1995 | Burdette et al. |
| 5,400,267 A | 3/1995 | Denen et al. |
| 5,423,220 A | 6/1995 | Finsterwald et al. |
| 5,423,811 A | 6/1995 | Imran et al. |
| 5,456,259 A | 10/1995 | Barlow et al. |
| 5,524,497 A | 6/1996 | Cavalloni |
| 5,558,672 A | 9/1996 | Edwards et al. |
| 5,575,788 A | 11/1996 | Baker et al. |
| 5,620,479 A | 4/1997 | Diederich |
| 5,630,837 A | 5/1997 | Crowley |
| 5,657,755 A | 8/1997 | Desai |
| 5,685,839 A | 11/1997 | Edwards et al. |
| 5,688,266 A | 11/1997 | Edwards et al. |
| 5,713,849 A | 2/1998 | Bosma et al. |
| 5,769,812 A | 6/1998 | Stevens et al. |
| 5,775,338 A | 7/1998 | Hastings |
| 5,800,482 A | 9/1998 | Pomeranz et al. |
| 5,803,083 A | 9/1998 | Buck et al. |
| 5,938,645 A | 8/1999 | Gordon |
| 6,066,134 A | 5/2000 | Eggers et al. |
| 6,097,985 A | 8/2000 | Kasevich et al. |
| 6,102,863 A | 8/2000 | Pflugrath et al. |
| 6,117,101 A | 9/2000 | Diederich et al. |
| 6,128,522 A | 10/2000 | Acker et al. |
| 6,149,596 A | 11/2000 | Bancroft |
| 6,190,377 B1 | 2/2001 | Kuzdrall |
| 6,216,704 B1 | 4/2001 | Ingle et al. |
| 6,254,598 B1 | 7/2001 | Edwards |
| 6,277,077 B1 | 8/2001 | Brisken et al. |
| 6,283,989 B1 | 9/2001 | Laufer et al. |
| 6,292,695 B1 | 9/2001 | Webster |
| 6,296,619 B1 | 10/2001 | Brisken et al. |
| 6,299,583 B1 | 10/2001 | Eggers et al. |
| 6,355,030 B1 | 3/2002 | Aldrich et al. |
| 6,383,151 B1 | 5/2002 | Diederich et al. |
| 6,475,149 B1 | 11/2002 | Frelburger et al. |
| 6,492,762 B1 | 12/2002 | Pant et al. |
| 6,514,249 B1 | 2/2003 | Maguire et al. |
| 6,517,534 B1 | 2/2003 | McGovern et al. |
| 6,529,756 B1 | 3/2003 | Phan |
| 6,547,788 B1 | 4/2003 | Maguire et al. |
| 6,564,096 B2 | 5/2003 | Mest |
| 6,584,360 B2 | 6/2003 | Francischelli et al. |
| 6,599,256 B1 | 7/2003 | Acker et al. |
| 6,599,288 B2 | 7/2003 | Maguire et al. |
| 6,635,054 B2 | 8/2003 | Maguire et al. |
| 6,607,502 B1 | 10/2003 | Fjield et al. |
| 6,645,202 B1 | 11/2003 | Pless et al. |
| 6,648,883 B2 | 11/2003 | Francischelli et al. |
| 6,669,655 B1 | 12/2003 | Acker |
| 6,692,490 B1 | 2/2004 | Edwards |
| 6,712,767 B2 | 3/2004 | Hossack et al. |
| 6,719,755 B2 | 4/2004 | Sliwa, Jr. et al. |
| 6,763,722 B2 | 7/2004 | Fjield et al. |
| 6,793,635 B2 | 9/2004 | Ryan et al. |
| 6,837,886 B2 | 1/2005 | Collins |
| 6,845,267 B2 | 6/2005 | Harrison et al. |
| 6,913,581 B2 | 7/2005 | Corl et al. |
| 6,953,469 B2 | 10/2005 | Ryan |
| 6,954,977 B2 | 10/2005 | Maguire |
| 6,978,174 B2 | 12/2005 | Gelfand et al. |
| 7,052,695 B2 | 5/2006 | Kalish |
| 7,156,816 B2 | 1/2007 | Schwartz et al. |
| 7,162,303 B2 | 1/2007 | Levin et al. |
| 7,285,116 B2 | 10/2007 | De la Rama et al. |
| 7,297,413 B2 | 11/2007 | Mitsumori |
| 7,347,852 B2 | 3/2008 | Hobbs et al. |
| 7,371,231 B2 | 5/2008 | Rioux et al. |
| 7,473,224 B2 | 1/2009 | Makin |
| 7,510,536 B2 | 5/2009 | Foley et al. |
| 7,540,846 B2 | 6/2009 | Harhen et al. |
| 7,617,005 B2 | 11/2009 | Demarais et al. |
| 7,620,451 B2 | 11/2009 | Demarais et al. |
| 7,621,873 B2 | 11/2009 | Owen et al. |
| 7,625,371 B2 | 12/2009 | Morris et al. |
| 7,647,115 B2 | 1/2010 | Levin et al. |
| 7,653,438 B2 | 1/2010 | Deem et al. |
| 7,678,104 B2 | 3/2010 | Keidar |
| 7,717,948 B2 | 5/2010 | Demarais et al. |
| 7,756,583 B2 | 7/2010 | Demarais et al. |
| 7,837,676 B2 | 11/2010 | Sinelnikov et al. |
| 7,847,317 B2 | 12/2010 | Maloney et al. |
| 7,873,417 B2 | 1/2011 | Demarais et al. |
| 7,937,143 B2 | 5/2011 | Demarais et al. |
| 7,942,871 B2 | 5/2011 | Thapliyal et al. |
| 8,024,050 B2 | 9/2011 | Libbus et al. |
| 8,131,371 B2 | 3/2012 | Demarais et al. |
| 8,137,274 B2 | 3/2012 | Weng et al. |
| 8,233,221 B2 | 7/2012 | Suijver et al. |
| 8,251,986 B2 | 8/2012 | Chornenky et al. |
| 8,287,472 B2 | 10/2012 | Ostrovksy et al. |
| 8,447,414 B2 | 5/2013 | Johnson et al. |
| 8,475,442 B2 | 7/2013 | Hall et al. |
| 8,483,831 B1 | 7/2013 | Hiavka et al. |
| 8,485,993 B2 | 7/2013 | Orszulak et al. |
| 8,504,147 B2 | 8/2013 | Deem et al. |
| D697,036 S | 1/2014 | Kay et al. |
| 8,626,300 B2 | 1/2014 | Demarais et al. |
| 8,702,619 B2 | 4/2014 | Wang |
| 8,715,209 B2 | 5/2014 | Gertner |
| 8,734,438 B2 | 5/2014 | Behnke |
| D708,810 S | 7/2014 | Lewis, Jr. |
| 8,774,913 B2 | 7/2014 | Demarais et al. |
| 8,790,281 B2 | 7/2014 | Diederich et al. |
| 8,808,345 B2 | 8/2014 | Clark et al. |

(56) References Cited

U.S. PATENT DOCUMENTS

| | | |
|---|---|---|
| 8,818,514 B2 | 8/2014 | Zarins et al. |
| D712,352 S | 9/2014 | George et al. |
| D712,353 S | 9/2014 | George et al. |
| D712,833 S | 9/2014 | George et al. |
| 8,845,629 B2 | 9/2014 | Demarais et al. |
| 8,932,289 B2 | 1/2015 | Mayse et al. |
| 8,974,445 B2 | 3/2015 | Warnking et al. |
| 9,022,948 B2 | 5/2015 | Wang |
| 9,028,472 B2 | 5/2015 | Mathur et al. |
| 9,066,720 B2 | 6/2015 | Ballakur et al. |
| 9,072,902 B2 | 7/2015 | Mathur et al. |
| 9,155,590 B2 | 10/2015 | Mathur |
| 9,186,198 B2 | 11/2015 | Demarais et al. |
| 9,186,212 B2 | 11/2015 | Nabulovsky et al. |
| 9,289,132 B2 | 3/2016 | Ghaffari |
| 9,326,816 B2 | 5/2016 | Srivastava |
| 9,327,123 B2 | 5/2016 | Yamasaki |
| 9,333,035 B2 | 5/2016 | Rudie |
| 9,339,332 B2 | 5/2016 | Srivastava |
| 9,345,530 B2 | 5/2016 | Ballakur et al. |
| 9,375,154 B2 | 6/2016 | Wang |
| 7,717,948 C1 | 8/2016 | Demarais et al. |
| 9,427,579 B2 | 8/2016 | Fain et al. |
| 9,439,598 B2 | 9/2016 | Shimada et al. |
| 9,649,064 B2 | 5/2017 | Toth et al. |
| 9,675,413 B2 | 6/2017 | Deem et al. |
| 9,700,372 B2 | 7/2017 | Schaer |
| 9,707,034 B2 | 7/2017 | Schaer |
| 9,723,998 B2 | 8/2017 | Wang |
| 9,730,639 B2 | 8/2017 | Toth et al. |
| 9,743,845 B2 | 8/2017 | Wang |
| 9,750,560 B2 | 9/2017 | Ballakur et al. |
| 9,770,291 B2 | 9/2017 | Wang et al. |
| 9,770,593 B2 | 9/2017 | Gross |
| 9,801,684 B2 | 10/2017 | Fain |
| 9,820,811 B2 | 11/2017 | Wang |
| 9,907,983 B2 | 3/2018 | Thapliyal et al. |
| 9,931,047 B2 | 4/2018 | Srivastava |
| 9,943,666 B2 | 4/2018 | Warnking |
| 9,956,034 B2 | 5/2018 | Toth et al. |
| 9,968,790 B2 | 5/2018 | Toth et al. |
| 9,981,108 B2 | 5/2018 | Warnking |
| 9,999,463 B2 | 6/2018 | Puryear et al. |
| 10,004,458 B2 | 6/2018 | Toth et al. |
| 10,004,557 B2 | 6/2018 | Gross et al. |
| 10,010,364 B2 | 7/2018 | Harringtpm |
| 10,016,233 B2 | 7/2018 | Pike |
| 10,022,085 B2 | 7/2018 | Toth et al. |
| 10,039,901 B2 | 8/2018 | Warnking |
| 10,123,903 B2 | 11/2018 | Warnking et al. |
| 10,143,419 B2 | 12/2018 | Toth et al. |
| 10,179,020 B2 | 1/2019 | Ballakur et al. |
| 10,179,026 B2 | 1/2019 | Ng |
| 10,182,865 B2 | 1/2019 | Naga et al. |
| 10,226,633 B2 | 3/2019 | Toth et al. |
| 10,245,429 B2 | 4/2019 | Deem et al. |
| 10,292,610 B2 | 5/2019 | Srivastava |
| 10,293,190 B2 | 5/2019 | Zarins et al. |
| 10,363,359 B2 | 7/2019 | Toth et al. |
| 10,368,775 B2 | 8/2019 | Hettrick et al. |
| 10,376,310 B2 | 8/2019 | Fain et al. |
| 10,383,685 B2 | 8/2019 | Gross et al. |
| 10,398,332 B2 | 9/2019 | Min et al. |
| 10,470,684 B2 | 11/2019 | Toth et al. |
| 10,478,249 B2 | 11/2019 | Gross et al. |
| 10,499,937 B2 | 12/2019 | Warnking |
| 10,543,037 B2 | 1/2020 | Shah |
| 10,850,091 B2 | 12/2020 | Zarins et al. |
| 11,185,662 B2 | 11/2021 | Warnking |
| 11,801,085 B2 | 10/2023 | Wu et al. |
| 2001/0007940 A1 | 7/2001 | Tu et al. |
| 2001/0023365 A1 | 9/2001 | Medhkour et al. |
| 2002/0002334 A1 | 1/2002 | Okuno et al. |
| 2002/0002371 A1 | 1/2002 | Acker et al. |
| 2002/0022833 A1 | 2/2002 | Maguire et al. |
| 2002/0042610 A1 | 4/2002 | Sliwa, Jr. et al. |
| 2002/0065512 A1 | 5/2002 | Fjield et al. |
| 2002/0072741 A1 | 6/2002 | Sliwa, Jr. et al. |
| 2002/0077594 A1* | 6/2002 | Chien ............... A61M 25/104 604/509 |
| 2002/0087156 A1 | 7/2002 | Maguire et al. |
| 2002/0150693 A1 | 10/2002 | Kobayashi et al. |
| 2002/0151889 A1 | 10/2002 | Swanson et al. |
| 2002/0156469 A1 | 10/2002 | Yon et al. |
| 2002/0165535 A1 | 11/2002 | Lesh |
| 2002/0173724 A1 | 11/2002 | Dorando et al. |
| 2002/0193681 A1 | 12/2002 | Vitek et al. |
| 2002/0193781 A1 | 12/2002 | Loeb |
| 2003/0004439 A1 | 1/2003 | Pant et al. |
| 2003/0028111 A1 | 2/2003 | Vaezy et al. |
| 2003/0060813 A1 | 3/2003 | Loeb et al. |
| 2003/0074039 A1 | 4/2003 | Puskas |
| 2003/0114878 A1 | 6/2003 | Diederich et al. |
| 2003/0125726 A1 | 7/2003 | Maguire et al. |
| 2003/0138571 A1 | 7/2003 | Kunishi et al. |
| 2003/0181963 A1 | 9/2003 | Pellegrino et al. |
| 2003/0204138 A1 | 10/2003 | Choi |
| 2003/0216721 A1 | 11/2003 | Diederich et al. |
| 2003/0216792 A1 | 11/2003 | Levin et al. |
| 2003/0216794 A1 | 11/2003 | Becker et al. |
| 2003/0225331 A1 | 12/2003 | Diederich et al. |
| 2003/0233099 A1 | 12/2003 | Danaek et al. |
| 2004/0019349 A1 | 1/2004 | Fuimaono et al. |
| 2004/0044286 A1 | 3/2004 | Hossack et al. |
| 2004/0082859 A1 | 4/2004 | Schaer |
| 2004/0097819 A1 | 5/2004 | Duarte |
| 2004/0106880 A1 | 6/2004 | Weng et al. |
| 2004/0122494 A1 | 6/2004 | Eggers et al. |
| 2004/0167415 A1 | 8/2004 | Gelfand et al. |
| 2004/0181178 A1 | 9/2004 | Aldrich et al. |
| 2004/0230116 A1 | 11/2004 | Cowan et al. |
| 2004/0242999 A1 | 12/2004 | Vitek et al. |
| 2004/0253450 A1 | 12/2004 | Seita et al. |
| 2005/0009218 A1 | 1/2005 | Kunihiro |
| 2005/0035901 A1 | 2/2005 | Lyon |
| 2005/0038340 A1 | 2/2005 | Vaezy et al. |
| 2005/0159738 A1 | 7/2005 | Visram et al. |
| 2005/0203501 A1 | 9/2005 | Aldrich et al. |
| 2005/0215990 A1 | 9/2005 | Govari |
| 2005/0228283 A1 | 10/2005 | Gifford et al. |
| 2005/0228459 A1 | 10/2005 | Levin et al. |
| 2005/0228460 A1 | 10/2005 | Levin et al. |
| 2005/0234523 A1 | 10/2005 | Levin et al. |
| 2005/0256518 A1 | 11/2005 | Rama et al. |
| 2005/0261672 A1 | 11/2005 | Deem et al. |
| 2005/0288730 A1* | 12/2005 | Deem ............... A61B 18/1206 607/42 |
| 2006/0041277 A1 | 2/2006 | Deem et al. |
| 2006/0052695 A1 | 3/2006 | Adam et al. |
| 2006/0058711 A1 | 3/2006 | Harhen et al. |
| 2006/0064081 A1 | 3/2006 | Rosinko |
| 2006/0088705 A1 | 4/2006 | Mitsumori |
| 2006/0100514 A1 | 5/2006 | Lopath |
| 2006/0118127 A1 | 6/2006 | Chinn |
| 2006/0121200 A1 | 6/2006 | Halpert et al. |
| 2006/0142827 A1 | 6/2006 | Willard et al. |
| 2006/0154072 A1 | 7/2006 | Schlossman et al. |
| 2006/0155269 A1 | 7/2006 | Warnking |
| 2006/0184069 A1 | 8/2006 | Vaitekunas |
| 2006/0184072 A1 | 8/2006 | Manna |
| 2006/0212076 A1 | 9/2006 | Demarais et al. |
| 2006/0212078 A1 | 9/2006 | Demarais et al. |
| 2006/0217772 A1 | 9/2006 | Libbus et al. |
| 2006/0229594 A1 | 10/2006 | Francischelli et al. |
| 2006/0235286 A1 | 10/2006 | Stone et al. |
| 2006/0241523 A1 | 10/2006 | Sinelnikov et al. |
| 2006/0265014 A1 | 11/2006 | Demarais et al. |
| 2006/0265015 A1 | 11/2006 | Demarais et al. |
| 2006/0270976 A1 | 11/2006 | Savage et al. |
| 2006/0276852 A1 | 12/2006 | Demarais et al. |
| 2007/0060921 A1 | 3/2007 | Janssen et al. |
| 2007/0072741 A1 | 3/2007 | Robideau |
| 2007/0106292 A1 | 5/2007 | Kaplan |
| 2007/0124458 A1 | 5/2007 | Kumar |

(56) References Cited

U.S. PATENT DOCUMENTS

| | | |
|---|---|---|
| 2007/0129720 A1 | 6/2007 | Demarais et al. |
| 2007/0129760 A1 | 6/2007 | Demarais et al. |
| 2007/0135875 A1* | 6/2007 | Demarais .............. A61N 1/28 607/96 |
| 2007/0173899 A1 | 7/2007 | Levin et al. |
| 2007/0175359 A1 | 8/2007 | Hwang |
| 2007/0203547 A1 | 8/2007 | Costello et al. |
| 2007/0203549 A1 | 8/2007 | Demarais et al. |
| 2007/0255267 A1 | 11/2007 | Diederich et al. |
| 2007/0255342 A1 | 11/2007 | Laufer |
| 2007/0265609 A1 | 11/2007 | Thapliyal et al. |
| 2007/0265610 A1 | 11/2007 | Thapliyal et al. |
| 2007/0265687 A1 | 11/2007 | Deem et al. |
| 2007/0282407 A1 | 12/2007 | Demarais et al. |
| 2007/0293762 A1 | 12/2007 | Sawada et al. |
| 2008/0039746 A1 | 2/2008 | Hissong et al. |
| 2008/0052186 A1 | 2/2008 | Walker et al. |
| 2008/0151001 A1 | 6/2008 | Sudo et al. |
| 2008/0215031 A1 | 9/2008 | Belfort et al. |
| 2008/0252172 A1 | 10/2008 | Yetter et al. |
| 2008/0255449 A1 | 10/2008 | Warnking et al. |
| 2008/0255478 A1 | 10/2008 | Burdette |
| 2008/0255642 A1 | 10/2008 | Zarins et al. |
| 2009/0024195 A1 | 1/2009 | Rezai et al. |
| 2009/0036948 A1 | 2/2009 | Levin et al. |
| 2009/0062873 A1 | 3/2009 | Wu et al. |
| 2009/0076409 A1 | 3/2009 | Wu et al. |
| 2009/0118125 A1 | 5/2009 | Kobayashi et al. |
| 2009/0118725 A1 | 5/2009 | Auth et al. |
| 2009/0124964 A1 | 5/2009 | Leach et al. |
| 2009/0149753 A1 | 6/2009 | Govari et al. |
| 2009/0171202 A1 | 7/2009 | Kirkpatrick et al. |
| 2009/0189485 A1 | 7/2009 | Iyoki |
| 2009/0204006 A1 | 8/2009 | Wakabayashi et al. |
| 2009/0221939 A1 | 9/2009 | Demarais et al. |
| 2009/0228003 A1 | 9/2009 | Sinelnikov |
| 2009/0234407 A1 | 9/2009 | Hastings et al. |
| 2009/0248005 A1 | 10/2009 | Rusin et al. |
| 2009/0248011 A1 | 10/2009 | Hlavka et al. |
| 2009/0299360 A1 | 12/2009 | Ormsby |
| 2009/0312673 A1 | 12/2009 | Thapliyal et al. |
| 2009/0312693 A1 | 12/2009 | Thapliyal et al. |
| 2009/0312755 A1 | 12/2009 | Thapliyal et al. |
| 2010/0016762 A1 | 1/2010 | Thapliyal et al. |
| 2010/0033940 A1 | 2/2010 | Yamaguchi et al. |
| 2010/0049099 A1 | 2/2010 | Thapliyal et al. |
| 2010/0113928 A1 | 5/2010 | Thapliyal et al. |
| 2010/0113985 A1 | 5/2010 | Thapliyal et al. |
| 2010/0114094 A1 | 5/2010 | Thapliyal et al. |
| 2010/0125198 A1 | 5/2010 | Thapliyal et al. |
| 2010/0130892 A1 | 5/2010 | Warnking |
| 2010/0137860 A1 | 6/2010 | Demarais et al. |
| 2010/0137952 A1 | 6/2010 | Demarais et al. |
| 2010/0152582 A1 | 6/2010 | Thapliyal et al. |
| 2010/0168731 A1* | 7/2010 | Wu .................... A61B 18/1206 606/33 |
| 2010/0168737 A1 | 7/2010 | Grunewald |
| 2010/0168739 A1 | 7/2010 | Wu et al. |
| 2010/0174282 A1 | 7/2010 | Demarais et al. |
| 2010/0179424 A1 | 7/2010 | Warnking et al. |
| 2010/0189974 A1 | 7/2010 | Ochi et al. |
| 2010/0191112 A1 | 7/2010 | Demarais et al. |
| 2010/0198065 A1 | 8/2010 | Thapliyal et al. |
| 2010/0249859 A1 | 9/2010 | Dilorenzo |
| 2010/0291722 A1 | 11/2010 | Kim |
| 2011/0004184 A1 | 1/2011 | Proksch et al. |
| 2011/0060324 A1 | 3/2011 | Wu et al. |
| 2011/0087096 A1 | 4/2011 | Behar |
| 2011/0087097 A1 | 4/2011 | Behar |
| 2011/0104060 A1 | 5/2011 | Seward |
| 2011/0112400 A1 | 5/2011 | Emery et al. |
| 2011/0118598 A1 | 5/2011 | Gertner |
| 2011/0118723 A1 | 5/2011 | Turner et al. |
| 2011/0125206 A1 | 5/2011 | Bornzin |
| 2011/0137298 A1 | 6/2011 | Nguyen et al. |
| 2011/0172527 A1 | 7/2011 | Gertner |
| 2011/0178516 A1 | 7/2011 | Orszulak et al. |
| 2011/0200171 A1 | 8/2011 | Beetel et al. |
| 2011/0208096 A1 | 8/2011 | Demarais et al. |
| 2011/0257523 A1 | 10/2011 | Hastings et al. |
| 2011/0257562 A1 | 10/2011 | Hastings et al. |
| 2011/0257563 A1 | 10/2011 | Schaer |
| 2011/0257564 A1 | 10/2011 | Thapliyal et al. |
| 2011/0257647 A1 | 10/2011 | Mayse et al. |
| 2011/0301662 A1 | 12/2011 | Bar-yoseph et al. |
| 2011/0319765 A1 | 12/2011 | Gertner et al. |
| 2012/0004656 A1 | 1/2012 | Jackson et al. |
| 2012/0065493 A1 | 3/2012 | Gertner |
| 2012/0065554 A1 | 3/2012 | Pikus |
| 2012/0078278 A1 | 3/2012 | Bales et al. |
| 2012/0095461 A1 | 4/2012 | Herscher et al. |
| 2012/0123243 A1 | 5/2012 | Hastings |
| 2012/0123303 A1 | 5/2012 | Sogard et al. |
| 2012/0143097 A1 | 6/2012 | Pike, Jr. |
| 2012/0165667 A1 | 6/2012 | Altmann et al. |
| 2012/0172723 A1 | 7/2012 | Gertner |
| 2012/0209118 A1 | 8/2012 | Warnking |
| 2012/0215106 A1 | 8/2012 | Sverdlik et al. |
| 2012/0232436 A1* | 9/2012 | Warnking .............. A61N 7/022 601/2 |
| 2012/0238918 A1 | 9/2012 | Gertner |
| 2012/0238919 A1 | 9/2012 | Gertner |
| 2012/0265198 A1 | 10/2012 | Crow et al. |
| 2012/0296232 A1 | 11/2012 | Ng |
| 2012/0316439 A1 | 12/2012 | Behar |
| 2013/0012844 A1 | 1/2013 | Demarais et al. |
| 2013/0023897 A1 | 1/2013 | Wallace |
| 2013/0085489 A1 | 4/2013 | Fain et al. |
| 2013/0090650 A1 | 4/2013 | Jenson et al. |
| 2013/0103064 A1 | 4/2013 | Arenson et al. |
| 2013/0110012 A1 | 5/2013 | Gertner |
| 2013/0116737 A1 | 5/2013 | Edwards et al. |
| 2013/0123770 A1 | 5/2013 | Smith |
| 2013/0131668 A1 | 5/2013 | Schaer |
| 2013/0131743 A1 | 5/2013 | Yamasaki et al. |
| 2013/0138018 A1 | 5/2013 | Gertner |
| 2013/0150749 A1 | 6/2013 | McLean et al. |
| 2013/0158441 A1 | 6/2013 | Demarais et al. |
| 2013/0158442 A1 | 6/2013 | Demarais et al. |
| 2013/0165822 A1 | 6/2013 | Demarais et al. |
| 2013/0165924 A1 | 6/2013 | Mathur et al. |
| 2013/0165925 A1 | 6/2013 | Mathur et al. |
| 2013/0197555 A1 | 8/2013 | Schaer |
| 2013/0204167 A1 | 8/2013 | Sverdlik et al. |
| 2013/0211396 A1 | 8/2013 | Sverdlik et al. |
| 2013/0218054 A1 | 8/2013 | Sverdlik et al. |
| 2013/0274614 A1 | 10/2013 | Shimada et al. |
| 2013/0274658 A1 | 10/2013 | Steinke et al. |
| 2013/0282084 A1 | 10/2013 | Mathur et al. |
| 2013/0289369 A1 | 10/2013 | Margolis |
| 2013/0289682 A1 | 10/2013 | Barman et al. |
| 2013/0304047 A1 | 11/2013 | Grunewald et al. |
| 2013/0331739 A1 | 12/2013 | Gertner |
| 2014/0012133 A1 | 1/2014 | Sverdlik et al. |
| 2014/0018788 A1 | 1/2014 | Engelman et al. |
| 2014/0018794 A1 | 1/2014 | Anderson et al. |
| 2014/0025069 A1 | 1/2014 | Willard et al. |
| 2014/0039477 A1 | 2/2014 | Sverdlik et al. |
| 2014/0046313 A1 | 2/2014 | Pederson et al. |
| 2014/0058294 A1 | 2/2014 | Gross et al. |
| 2014/0067029 A1 | 3/2014 | Schauer et al. |
| 2014/0074083 A1 | 3/2014 | Horn et al. |
| 2014/0107482 A1 | 4/2014 | Warnking |
| 2014/0107639 A1 | 4/2014 | Zhang et al. |
| 2014/0163540 A1 | 6/2014 | Iyer et al. |
| 2014/0180196 A1 | 6/2014 | Stone et al. |
| 2014/0180197 A1 | 6/2014 | Sverdlik et al. |
| 2014/0194785 A1 | 7/2014 | Gertner |
| 2014/0200489 A1 | 7/2014 | Behar et al. |
| 2014/0214018 A1 | 7/2014 | Behar et al. |
| 2014/0249524 A1 | 9/2014 | Kocur |
| 2014/0257271 A1 | 9/2014 | Mayse et al. |
| 2014/0272110 A1 | 9/2014 | Taylor et al. |
| 2014/0274614 A1 | 9/2014 | Min et al. |

(56) References Cited

U.S. PATENT DOCUMENTS

| | | |
|---|---|---|
| 2014/0275924 A1 | 9/2014 | Min et al. |
| 2014/0276742 A1 | 9/2014 | Nabutovsky et al. |
| 2014/0276752 A1 | 9/2014 | Wang et al. |
| 2014/0276755 A1 | 9/2014 | Cao et al. |
| 2014/0276789 A1 | 9/2014 | Dandler et al. |
| 2014/0277033 A1 | 9/2014 | Taylor et al. |
| 2014/0288551 A1 | 9/2014 | Bharmi et al. |
| 2014/0288616 A1 | 9/2014 | Rawat et al. |
| 2014/0303617 A1 | 10/2014 | Shimada |
| 2015/0025518 A1 | 1/2015 | Kobayashi et al. |
| 2015/0105715 A1 | 4/2015 | Pikus et al. |
| 2015/0111918 A1 | 4/2015 | Sobotka et al. |
| 2015/0223877 A1 | 8/2015 | Behar et al. |
| 2015/0289931 A1 | 10/2015 | Puryear et al. |
| 2015/0335919 A1 | 11/2015 | Behar et al. |
| 2016/0000345 A1 | 1/2016 | Kobayashi et al. |
| 2016/0016016 A1 | 1/2016 | Behar et al. |
| 2016/0045121 A1 | 2/2016 | Akingba et al. |
| 2016/0175582 A1 | 6/2016 | Serna |
| 2016/0331459 A1 | 11/2016 | Townley |
| 2017/0027460 A1 | 2/2017 | Shimada et al. |
| 2017/0035310 A1 | 2/2017 | Shimada et al. |
| 2017/0296264 A1 | 10/2017 | Wang |
| 2018/0022108 A1 | 1/2018 | Mori et al. |
| 2018/0042670 A1 | 2/2018 | Wang et al. |
| 2018/0064359 A1 | 3/2018 | Pranaitis |
| 2018/0078307 A1 | 3/2018 | Wang et al. |
| 2018/0185091 A1 | 7/2018 | Toth et al. |
| 2018/0221087 A1 | 8/2018 | Puryear et al. |
| 2018/0249958 A1 | 9/2018 | Toth et al. |
| 2018/0250054 A1 | 9/2018 | Gross et al. |
| 2018/0280082 A1 | 10/2018 | Puryear et al. |
| 2018/0289320 A1 | 10/2018 | Toth et al. |
| 2018/0310991 A1 | 11/2018 | Pike |
| 2018/0333204 A1 | 11/2018 | Ng |
| 2019/0046111 A1 | 2/2019 | Toth et al. |
| 2019/0046264 A1 | 2/2019 | Toth et al. |
| 2019/0076191 A1 | 3/2019 | Wang |
| 2019/0110704 A1 | 4/2019 | Wang |
| 2019/0134396 A1 | 5/2019 | Toth et al. |
| 2019/0151670 A1 | 5/2019 | Toth et al. |
| 2019/0183560 A1 | 6/2019 | Ballakur et al. |
| 2019/0307361 A1 | 10/2019 | Hettrick et al. |
| 2020/0046248 A1 | 2/2020 | Toth et al. |
| 2020/0077907 A1 | 3/2020 | Shimada et al. |

FOREIGN PATENT DOCUMENTS

| | | |
|---|---|---|
| EP | 0659387 A1 | 6/1995 |
| EP | 0767630 | 4/1997 |
| EP | 0774276 A2 | 5/1997 |
| EP | 0838980 | 4/1998 |
| EP | 1042990 A1 | 10/2000 |
| EP | 1100375 | 5/2001 |
| EP | 1384445 | 1/2004 |
| EP | 1579889 | 9/2005 |
| EP | 1598024 A2 | 11/2005 |
| EP | 1647305 | 4/2006 |
| EP | 2218479 | 8/2010 |
| EP | 2359764 | 8/2011 |
| EP | 2430996 | 3/2012 |
| EP | 2457614 | 5/2012 |
| EP | 2460486 | 6/2012 |
| EP | 2495012 | 9/2012 |
| EP | 1503685 | 10/2012 |
| EP | 2521593 | 11/2012 |
| EP | 1299035 | 2/2013 |
| EP | 2561903 | 2/2013 |
| EP | 2561905 | 2/2013 |
| EP | 2626022 | 8/2013 |
| EP | 2632373 | 9/2013 |
| EP | 2662041 | 11/2013 |
| EP | 2662043 | 11/2013 |
| EP | 2842604 | 3/2015 |
| EP | 2968984 | 8/2016 |
| EP | 2995250 | 10/2019 |
| EP | 3799931 | 4/2021 |
| GB | 2037166 A | 7/1980 |
| JP | 05-068684 | 3/1993 |
| JP | 07-178173 | 7/1995 |
| JP | 40-826437 | 10/1996 |
| JP | 10-127678 | 5/1998 |
| JP | 10-507229 | 7/1998 |
| JP | 11-218100 | 8/1999 |
| JP | 2000-054153 | 2/2000 |
| JP | 2001-011126 | 4/2001 |
| JP | 2002-078809 | 3/2002 |
| JP | 2006-161116 | 6/2006 |
| JP | 2008-214669 | 9/2008 |
| JP | 2011-219828 | 11/2011 |
| WO | WO 90/00420 A1 | 1/1990 |
| WO | WO 92/07622 A1 | 5/1992 |
| WO | WO 92/20291 A1 | 11/1992 |
| WO | WO 94/05365 A1 | 3/1994 |
| WO | WO 94/11057 A1 | 5/1994 |
| WO | WO 95/19143 A1 | 7/1995 |
| WO | WO 95/25472 A1 | 9/1995 |
| WO | WO 96/00039 A1 | 1/1996 |
| WO | WO 97/13463 A1 | 4/1997 |
| WO | WO 97/36548 A1 | 10/1997 |
| WO | WO 98/41178 A1 | 9/1998 |
| WO | WO 98/42403 A1 | 10/1998 |
| WO | WO 98/49957 A1 | 11/1998 |
| WO | WO 98/52465 A1 | 11/1998 |
| WO | WO-99/02096 | 1/1999 |
| WO | WO 99/35987 A1 | 7/1999 |
| WO | WO 99/44519 A1 | 9/1999 |
| WO | WO 99/52423 A1 | 10/1999 |
| WO | WO 99/56812 A1 | 11/1999 |
| WO | WO 00/16850 A1 | 3/2000 |
| WO | WO 00/27292 A1 | 5/2000 |
| WO | WO 00/041881 | 7/2000 |
| WO | WO 00/42934 A1 | 7/2000 |
| WO | WO 00/51511 A1 | 9/2000 |
| WO | WO 00/51683 A1 | 9/2000 |
| WO | WO 00/56237 A2 | 9/2000 |
| WO | WO 00/57495 A1 | 9/2000 |
| WO | WO 00/67648 A1 | 11/2000 |
| WO | WO 00/67656 A1 | 11/2000 |
| WO | WO 00/67659 A1 | 11/2000 |
| WO | WO 00/67830 A1 | 11/2000 |
| WO | WO 00/67832 A2 | 11/2000 |
| WO | WO 01/13357 A1 | 2/2001 |
| WO | WO 01/22897 A1 | 4/2001 |
| WO | WO 01/37925 A2 | 5/2001 |
| WO | WO 01/70114 A1 | 9/2001 |
| WO | WO 01/80723 A2 | 11/2001 |
| WO | WO 01/82814 A1 | 11/2001 |
| WO | WO 01/95820 A1 | 12/2001 |
| WO | WO 02/05868 A1 | 1/2002 |
| WO | WO 02/005897 | 1/2002 |
| WO | WO 2002/019934 | 3/2002 |
| WO | WO 02/083196 A1 | 10/2002 |
| WO | WO 02/085192 A1 | 10/2002 |
| WO | WO 03/003930 A1 | 1/2003 |
| WO | WO 03/022167 | 3/2003 |
| WO | WO 03/051450 | 6/2003 |
| WO | WO 03/059437 | 7/2003 |
| WO | WO 03/099382 | 12/2003 |
| WO | WO 2004/023978 A1 | 3/2004 |
| WO | WO 2004/091255 | 10/2004 |
| WO | WO-2005/009218 | 2/2005 |
| WO | WO-2006/041847 | 4/2006 |
| WO | WO-2006/041881 | 4/2006 |
| WO | WO-2006/060053 | 6/2006 |
| WO | WO 2007/014003 | 2/2007 |
| WO | WO-2007/124458 | 11/2007 |
| WO | WO-2007/135875 | 11/2007 |
| WO | WO-2007/146834 | 12/2007 |
| WO | WO-2008/003058 | 1/2008 |
| WO | WO-2008/036479 | 3/2008 |
| WO | WO-2008/052186 | 5/2008 |
| WO | WO-2008/061152 | 5/2008 |
| WO | WO-2008/151001 | 12/2008 |

(56) References Cited

FOREIGN PATENT DOCUMENTS

| | | |
|---|---|---|
| WO | WO-2009/149315 | 12/2009 |
| WO | WO-2010/033940 | 3/2010 |
| WO | WO-2010/067360 | 6/2010 |
| WO | WO-2011/046880 | 4/2011 |
| WO | WO-2011/053757 | 5/2011 |
| WO | WO-2011/082279 | 7/2011 |
| WO | WO-2011/088399 | 7/2011 |
| WO | WO-2011/094367 | 8/2011 |
| WO | WO-2011/139589 | 11/2011 |
| WO | WO-2012/112165 | 8/2012 |

OTHER PUBLICATIONS

Avitall, B., et al. "The creation of linear continuous lesions in the atria with an expandable loop catheter." J Am Coll Cardiol, 33,4:972-974 (1999).
Bartlett, T.G., et al. "Current management of the Wolff-Parkinson-White syndrome." J Card Surg. 8:503-515 (1993).
Benito, F., et al. "Radio frequency catheter ablation of accessory pathways in infants," Heart, 78:160-162 (1997).
Bhatt, et al., A Controlled Trial of Renal Denervation for Resistant Hypertension, N. Engl. J. Med., 370:1393-1401 (2014).
Blumenfeld, J.D., et al. "13-Adrenergic receptor blockade as a therapeutic approach for suppressing the renin-angiotensin-aldosterone system in normotensive and hypertensive subjects." AJH, 12:451-459 (1999).
Bunch, Jared, et al., Mechanisms of Phrenic Nerve Injury During Radiofrequency Ablation at the Pulmonary Vein Orifice, Journal of Cardiovascular Electrophysiology, 16(12): 1318-1325 (2005).
Callans, D. J. "Narrowing of the superior vena cava—right atrium junction during radiofrequency catheter ablation for inappropriate sinus tachycardia: Analysis with intracardiac echocardiography." JACC, 33:1667-1670 (1999).
Campese, et al., Renal afferent denervation prevents hypertension in rats with chronic renal failure, Hypertension, 25:878-882 (1995).
Cao, H., et al. "Flow effect on lesion formation in RF cardiac catheter ablation." IEEE T Bio-Med Eng, 48:425-433 (2001).
Chen, S.-A., et al. "Complications of diagnostic electrophysiologic studies and radiofrequency catheter ablation in patients with tachyarrhythmias: An eight-year survey of 3,966 consecutive procedures in a tertiary referral center." Am J Cardiol, 77:41-46 (1996).
Chen, Shih-Ann, M.D., "Initiation of Atrial Fibrillation by Ectopic Beats Originating From the Pulmonary Veins," Circulation 100(18): 1879-86, 1999.
Chinitz, et al., "Mapping Reentry Around Atriotomy Scars Using Double Potentials," Pacing and Clinical Electrophysiology, Cardiostim 96 Proceedings, Part II, vol. 19: 1978-1983 (1996).
Cioni, R., et al. "Renal artery stenting in patients with a solitary functioning kidney." Cardiovasc Intervent Radiol, 24:372-377 (2001).
Cosby, R.L., et al. "The role of the sympathetic nervous system and vasopressin in the pathogenesis of the abnormal sodium and water." Nefrologia, V, 4:271-277 (1985).
Cosio, Francisco G., "Atrial Flutter Mapping and Ablation II," Pacing & Clin. Electrophysiol. 19(6):965-75, 1996.
Cox, J.L. "The status of surgery for cardiac arrhythmias." Circulation, 71 :413-417 (1985).
Cox, J.L. et al. "Five-year experience with the Maze procedure for atrial fibrillation." Ann Thorac Surg, 56:814-824 (1993).
Cruickshank, J.M. "Beta-blockers continue to surprise us." Eur Heart J, 21 :354-364 (2000).
Curtis, J.J., et al. "Surgical therapy for persistent hypertension after renal transplantation," Transplantation, 31:125-128 (1981).
Demazumder, D., et al. "Comparison of irrigated electrode designs for radiofrequency ablation of myocardium." J Interv Card Electr, 5:391-400 (2001 ).
Di Bona, G.F. "Neural control of the kidney: Functionally specific renal sympathetic nerve fibers." Am J Physiol Regulatory Integrative Comp Physiol, 279:R1517-R1524 (2000).

Dibona, Renal nerves in compensatory renal response to contralateral renal denervation, Renal Physiology, 238 (1 ):F26-F30 (1980).
DiBona, G.F. "Sympathetic nervous system and kidney in hypertension," Nephrol and Hypertension, 11: 197-200 (2002).
DiBona, G.F., et al. "Neural control of renal function," Physiol Rev, 77:75-197 (1997).
Di Bona, G.F., et al. "Renal hemodynamic effects of activation of specific renal sympathetic nerve fiber groups." Am J Physiol Regul Integr Comp Physiol, 276:R539-R539 (1999).
Diederich C.J. et al. "Transurethral Ultrasound Array for Prostate Thermal Therapy: Initial Studies", IEEE Transactions on Ultrasonic, Ferroelectronics And Frequency Control IEEEE USA, vol. 43 No. 6 Nov. 1996 pp. 1011-1022.
Doggrell, S.A., et al. "Rat models of hypertension, cardiac hypertrophy and failure." Cardiovasc Res, 39:89-105 (1998).
Dong Q., et al. "Diagnosis of renal vascular disease with MR angiography." RadioGraphies, 19:1535-1554 (1999).
Dubuc, M., et al. "Feasibility of cardiac cryoablation using a transvenous steerable electrode catheter," J Interv Cardiac Electrophysiol, 2:285-292 (1998).
Extended European Search Report, Application No. EP 10 72 9496, dated Jul. 25, 2012.
Extended EP Search Report dated Dec. 5, 2016 in EP Patent Application Serial No. 16183988.1.
Extended European Search Report dated Feb. 15, 2016 in EP Patent Application Serial No. 15182333.3.
Extended European Search Report dated Feb. 17, 2016 in EP Patent Application Serial No. 14 775754.6.
Feld, Gregory K., "Radiofrequency Catheter Ablation for the Treatment of Human Type I Atrial Flutter," Circulation, 86(3):1233-1240 (1992).
Gallagher, John J., "Wolff-Parkinson-White Syndrome: Surgery to Radiofrequency Catheter Ablation," 1997.
Gilard, M., et al. "Angiographic anatomy of the coronary sinus and its tributaries." PACE, 21 :2280-2284 (1998).
Gorisch, W., et al. "Heat-induced contraction of blood vessels." Lasers Surg Med, 2:1-13 (1982).
Haines, D.E. et al. "Tissue heating during radiofrequency catheter ablation; A thermodynamic model and observations in isolated perfused and superfused canine right ventricular free wall." PACE, 12:962-976 (1989).
Haissaguerre, et al., "Radiofrequency Catheter Ablation in Unusual Mechanisms of Atrial Fibrillation," Journal of Cardiovascular Electrophysiology, 5(9):743-1751 (1994).
Haissaguerre, et al., "Right and Left Atrial Radiofrequency Catheter Therapy of Paroxysmal Atrial Fibrillation," Journal of Cardiovascular Electrophysiology, 7(12):1133-1144 (1996).
Haissaguerre, Michel, "Electrophysiological End Point for Catheter Ablation of Atrial Fibrillation Initiated From Multiple Venous Foci," Circulation, 101: 1409-1417 (2000).
Haissaguerre, Michel, M.D., "Predominant Origin of Atrial Panarrhythmic Triggers in the Pulmonary Veins: A Distinct Electrophysiologic Entity," 1997.
Haissaguerre, Michel, M.D., et al., "Spontaneous Initiation of Atrial Fibrillation by Ectopic Beats Originating in the Pulmonary Veins," The New England Journal of Medicine, 339(10):659-666 (1998).
Han, Y.-M., et al. "Renal artery embolization with diluted hot contrast medium: An experimental study," J Vasc Interv Radiol, 12:862-868 (2001).
Hatala, Robert, "Radiofrequency Catheter Ablation of Left Atrial Tachycardia Originating Within the Pulmonary Vein in a Patient with Dextrocardia," Pacing and Clinical Electrophysiology, 19(6):999-1002 (1996).
Hindricks, G. "The Multicentre European Radiofrequency Survey (MERFS): Complications of radiofrequency catheter ablation of arrhythmias." Eur Heart J, 14:1644-1653 (1993).
Ho, S.Y., et al. "Architecture of the pulmonary veins: Relevance to the radiofrequency ablation." Heart 86:265-270 (2001).
Hocini, et al., "Concealed Left Pulmonary Vein Potentials Unmasked by Left Atrial Stimulation," Pacing and Clinical Electrophysiology, 23(11):1828-1831, part 2 (2000).

(56) References Cited

OTHER PUBLICATIONS

Hocini, et al., "Multiple Sources initiating Atrial Fibrillation from a Single Pulmonary Vein Identified by a Circumferential Catheter," Pacing and Clinical Electrophysiology, 23(11 ): 1828-1831, Part 2 (2000).

Hsieh, et al., "Double Multielectrode Mapping Catheters Facilitate Radiofrequency Catheter Ablation of Focal Atrial Fibrillation Originating from Pulmonary Veins," Journal of Cardiovascular Electrophysiology, 10(2):136-144 (1999).

Huang et al., "Renal denervation prevents and reverses hyperinsulinemia-induced hypertension in rats," Hypertension 32, pp. 249-254 (1998).

Huang, S.K.S., et al. "Radiofrequency catheter ablation of cardiac arrhythmias: Basic concepts and clinical applications." 2nd ed. Armonk, NY: Futura Publishing Co. (2000).

Igawa, et al., "The Anatomical Features of the Junction between the Left Atrium and the Pulmonary Veins: The Relevance with Atrial Arrhythmia", Circulation, Journal of the American Heart Association, Abstracts from the 72nd Scientific Sessions, 100(18):1-285 (1999).

International Search Report for PCT/US2010//020333 dated Feb. 25, 2010.

International Search Report, Application No. PCT/US01/22237 dated Sep. 19, 2002.

International Search Report, Application No. PCT/US04/05197 dated Apr. 12, 2005.

International Search Report, Application No. PCT/US07/11346 dated Jan. 9, 2008.

International Search Report, Application No. PCT/US2001/022221 dated Jan. 3, 2002.

International Search Report & Written Opinion dated Jul. 9, 2014 in Int'l PCT Patent Appl. Serial No. PCT/US2014/22804.

International Search Report & Written Opinion dated Nov. 29, 2011 in Int'l PCT Patent Appl. Serial No. PCT/US2011/025543.

International Search Report dated Feb. 9, 2014 in Int'l PCT Patent Appl. Serial No. PCT/US2014/022796.

International Search Report dated Jul. 9, 2014 in Int'l PCT Patent Appl. Serial No. PCT/US2014/22804.

Jackman, W.M., et al. "Treatment of supraventricular tachycardia due to atrioventricular nodal reentry by radiofrequency catheter ablation of slow-pathway conduction." N England J Med, 327, 5:313-318 (Jul. 30, 1992).

Jain, M.K., et al. "A three-dimensional finite element model of radiofrequency ablation with blood flow and its experimental validation." Ann Biomed Eng, 28:1075-1084 (2000).

Jais, Pierre, M.D., "A Focal Source of Atrial Fibrillation Treated by Discrete Radiofrequency Ablation," Circulation, 95(3):572-576 (1996).

Kapural, L., et al. "Radiofrequency ablation for chronic pain control." Curr Pain Headache Rep, 5 :517-525 (2001).

Kay, et al., "Radiofrequency Ablation for Treatment of Primary Atrial Tachycardia," Journal of the American College of Cardiology, 21 (4):901-909 (1993).

Koepke, J.P., et al. "The physiology teacher: Functions of the renal nerves." The Physiologist, 28, 1:47-52 (1985).

Kompanowska-Jezierska, et al. "Early effects of renal denervation in the anaesthetised rat: Natriuresis and increased cortical blood flow," J Physiol, 531.2:527-534 (2001).

Krimholtz et al., "New Equivalent Circuits for Elementary Piezoelectric Transducers," Electronics Lettres, vol. 6, No. 13, pp. 398-399, Jun. 25, 1970.

Kumagai, et al., "Treatment of Mixed Atrial Fibrillation and Typical Atrial Flutter by Hybrid Catheter Ablation," Pacing and Clinical Electrophysiology, 23(11 ):1839-1842, Part 2 (2000).

Labonte, S. "Numerical model for radio-frequency ablation of the endocardium and its experimental validation." IEEE T Bio-med Eng, 41,2:108-115 (1994).

Lee, S.-J., et al. "Ultrasonic energy in endoscopic surgery," Yonsei Med J, 40:545-549 (1999).

Leertouwer, Tic., et al. "In-vitro validation, with histology, of intravascular ultrasound in renal arteries." J Hypertens, 17:271-277 (1999).

Lesh, M.D., "An Anatomic Approach to Prevention of Atrial Fibrillation: Pulmonary Vein Isolation with Through-the-Balloon Ultrasound Ablation (TTB-US)," Thorac. Cardiovasc. Surg. 4 7 (1999) (Suppl.) 34 7-51.

Lesh, Michael D., M.D., "Radiofrequency Catheter Ablation of Atrial Arrhythmias," Circulation, 89(3) : 1074-1089 (1994).

Levin, H.R., et al. "Modulation of renal nerve to treat CHF." U.S. Appl. No. 60/370,190, filed 2002.

Liem, L. Bing, "In Vitro and In Vivo Results of Transcatheter Microwave Ablation Using Forward-Firing Tip Antenna Design," Pacing and Clinical Electrophysiology, Cardiostim '96 Proceedings, 19(11), Part 2 pp. 2004-2008 (1996).

Lin, Wei-Shiang, M.D., "Pulmonary Vein Morphology in Patients with Paroxysmal Atrial Fibrillation Initiated by Ectopic Beats Originating From the Pulmonary Veins," Circulation 101 (11):1274-81, 2000.

Lowe, J.E. "Surgical treatment of the Wolff-Parkinson-White syndrome and other supraventricular tachyarrhythmias." J Card Surg, 1:117-134 (1986).

Lundin, S. et al. "Renal sympathetic activity in spontaneously hypertensive rats and normotensive controls, as studied by three different methods." Acta Physiol Scan, 120,2:265-272 (1984).

Lustgarten, D.L., et al. "Cryothermal ablation: Mechanism of tissue injury and current experience in the treatment of tachyarrhythmias," Progr Cardiovasc Dis, 41 :481-498 (1999).

Mallavarapu, Christopher, "Radiofrequency Catheter Ablation of Atrial Tachycardia with Unusual Left Atrial Sites of Origin," Pacing and Clinical Electrophysiology, vol. 19(6), pp. 988-992 (1996).

McRury, I.D., et al. "Nonuniform heating during radiofrequency catheter ablation with long electrodes." Circulation, 96:4057-4064 (1997).

Medtronic Announces U.S. Renal Denervation Pivotal Trial Fails to Meet Primary Efficacy Endpoint While Meeting Primary Safety Endpoint, Medtronic Press Release, Jan. 9, 2014.

Mehdirad, A., et al. "Temperature controlled RF ablation in canine ventricle and coronary sinus using 7 Fr or 5 Fr ablation electrodes." PACE, 21:310-321 (1998).

Miller, B.F., and Keane, C.B. "Miller-Keane Encyclopedia & Dictionary of Medicine, Nursing, & Allied Health." Philadelphia: Saunders (1997) ("ablation").

Misaki, T., et al. "Surgical treatment of patients with Wolff-ParkinsonWhite syndrome and associated Ebstein's anomaly." J Thoracic Cardiovase Surg, 110: 1702-1707 (1995).

Moak, J.P., et al. "Case report: Pulmonary vein stenosis following RF ablation of paroxysmal atrial fibrillation: Successful treatment with balloon dilation." J Interv Card Electrophys, 4:621-631 (2000).

Montenero, Sandro, Annibale, "Electrograms for Identification of the Atrial Ablation Site During Catheter Ablation of Accessory Pathways," Pacing and Clinical Electrophysiology, vol. 19(6), pp. 905-912 (1996).

Morrissey, D.M., "Sympathectomy in the treatment of hypertension." Lancet, CCLXIV:403-408 (1953).

Moubarak, Jean B., "Pulmonary Veins-Left Atrial Junction: Anatomic and Histological Study," Pacing & Clin. Electrophys. 23(11 pt. 2):1836-8, 2000.

Nakagawa, A., et al. "Selective ablation of porcine and rabbit liver tissue using radiofrequency: Preclinical study." Eur Surg Res, 31:371-379 (1999).

Nakagawa, H., et al. "Comparison of in vivo tissue temperature profile and lesion geometry for radiofrequency ablation with a saline-irrigated electrode versus temperature control in a canine thigh muscle preparation." Circulation, 91 :2264-2273 (1995).

Nakagawa, H., et al. "Inverse relationship between electrode size and lesion size during radiofrequency ablation with active electrode cooling." Circulation, 98:458-465 (1998).

Neutel, J. M. "Hypertension and its management: A problem in need of new treatment strategies." JRAAS, I:S 1 O-S 13 (2000).

Nozawa, T., et al. "Effects of long-term renal sympathetic denervation on heart failure after myocardial infarction in rats." Heart Vessels, 16:51-56 (2002).

O'Connor, B.K., et al. "Radiofrequency ablation of a posteroseptal accessory pathway via the middle cardiac vein in a six-year-old child." PACE, 20:2504-2507 (1997).

(56) References Cited

OTHER PUBLICATIONS

Oliveira et al., "Renal Denervation Normalizes Pressure and Baroreceptor Reflex in High Renin Hypertension in Conscious Rats," Hypertension Suppl. 11 vol. 19 No. 2 pp. 17-21 (1992).
OnlineMathLearning.com, Volume Formula, "Volume of a Hollow Cylinder", Oct. 24, 2008.
Oral, H., et al. "Pulmonary vein isolation for paroxysmal and persistent atrial fibrillation." Circulation, 105: 1077-1081 (2002).
Page, I., et al. "The effect of renal denervation in the level of arterial blood pressure and renal function in essential hypertension." J Clin Invest, XIV:27-30 (1935).
Panescu, D., et al. "Radiofrequency multielectrode catheter ablation in the atrium." Phys Med Biol, 44:899-915 (1999).
Partial European Search Report, Application No. 10 01 0582, dated Sep. 20, 2011.
Partial Supplementary European Search Report, Application No. EP 01 95 2750, dated Aug. 15, 2005.
Pavin, D., et al. "Permanent left atrial tachycardia: Radiofrequency catheter ablation through the coronary sinus." J Cardiovasc Electrophysiol, 12:395-398 (2002).
Peet, M., "Hypertension and its surgical treatment by bilateral supradiaphragmatic splanchnicectomy," Am. J. Surgery, pp. 48-68 (1948).g.
Petersen, H. H., et al. "Lesion dimensions during temperature controlled radiofrequency catheter ablation of left ventricular porcine myocardium: Impact of ablation site, electrode size, and convective cooling." Circulation, 99:319-325 (1999).
Pohl, M.A. "Renovascular hypertension and ischemic nephropathy" A chapter in a book edited by Sehrier, R.W. "Atlas of diseases of the kidney: Hypertension and the kidney." Blackwell Science (1999).
Prager, Nelson, A., "Long Term Effectiveness of Surgical Treatment of Ectopic Atrial Tachycardia," Journal of the American College of Cardiology, vol. 22(1 ):85-92 (1993).
Pugsley, M.K., et al. "The vascular system" An overview of structure and function. J Pharmacol Toxical Methods, 44:333-340 (2000).
Rappaport et al. "Wide-Aperture Microwave Catheter-Based Cardiac Ablation", Proceedings of the First Joint BMES/EMBS Conference, Oct. 13-16, 1999, p. 314.
Response to Written Opinion under Article 34 for PCT/US2010/020333, filed Nov. 8, 2010, 13 pages.
Reuter, David, M.D., et al., "Future Directions of Electrotherapy for Atrial Fibrillation," Journal of Cardiovascular Electrophysiology, 9(8):S202-S210 (1998).
Robbins, Ivan, M.D., "Pulmonary Vein Stenosis After Catheter Ablation of Atrial Fibrillation," Circulation, 98:1769-1775 (1998).
Sanderson, J.E., et al. "Effect of B-blockage on baroreceptor and autonomic function in heart failure." Clin Sei, 69:137-146 (1999).
Schauerte, P., et al. "Catheter ablation of cardiac autonomic nerves for prevention of vagal atrial fibrillation," Circulation, 102:2774-2780 (2000).
Scheinman, M. M., et al. "The 1998 NASPE prospective catheter ablation registry." PACE, 23:1020-1028 (2000).
Scheinman, Melvin M., "NASPE Survey on Catheter Ablation," 1995.
Smithwick et al., "Splanchnicetomy for Essential Hypertension," J. Am. Med. Assn. 152:16, pp. 1501-1504 (1953).
Smithwick, R.H., Surgery in hypertension, Lancet, 2:65 (1948).
Smithwick, R.H., Surgical treatment of hypertension, Am. J. Med. 4:744-759 (1948).
Solis-Herruzo et al., "Effects Lumbar Sympathetic Block on Kidney Function in Cirrhotic Patients with Hepatorneal Syndrome," J. Hepatol. 5, pp. 167-173 (1987).
Stella, A., et al. "Effects of reversible renal denervation on hemodynamic and excretory functions of the ipsilateral and contralateral kidney in the cat," J Hypertension, 4: 181-188 (1986).
Stellbrink, C., et al. "Transcoronary venous radiofrequency catheter ablation of ventricular tachycardia." J Cardiovasc Electropysiol 8:916-921 (1997).

Supplementary European Search Report, Application No. EP 01 952 746.4, dated Feb. 24, 2005.
Supplementary European Search Report, Application No. EP 01 952 750.6, dated Dec. 6, 2005.
Supplementary European Search Report, Application No. EP 07 77 6968, dated Jan. 25, 2010.
Swain, et al., An endoscopically deliverable tissue-transfixing device for securing biosensors in the gastrointestinal tract, Gastrointestinal Endoscopy. 1994, 40:AB35.
Swartz, John F., "A Catheter-based Curative Approach to Atrial Fibrillation in Humans," Circulation, Abstracts from the 67th Scientific Sessions, Clinical Cardiology: Radio Frequency Ablation of Atrial Arrhythmias, 90(4), part 2, 1-335 (1994).
Swartz, John F., M.D., "Radiofrequency Endocardial Catheter Ablation of Accessory Atrioventricular Pathway Atrial Insertion Sites," Circulation, 87:487-499 (1993).
Takahashi, H., et al. "Retardation of the development of hypertension in DOCA-salt rats by renal denervation." Jpn Circ J, 48:567-574 (1984).
Tanaka et al., "A new radiofrequency thermal balloon catheter for pulmonary vein isolation," Journal of the American College of Cardiology 38(7): 2079-86, Dec. 2001.
Tracy, Cynthia M., "Radiofrequency Catheter Ablation of Ectopic Atrial Tachycardia Using Paced Activation Sequence Mapping," J. of the Amer. College of Cardiol. 21(4):910-7, 1993.
Tungjitkusolmun, S. "Ablation." A chapter in a book edited by Webster, J. G., "Minimally invasive medical technology." Bristol UK: IOP Publishing, 219 (2001).
Uchida, F., et al. "Effect of radio frequency catheter ablation on parasympathetic denervation: A comparison of three different ablation sites," PACE, 21 :2517-2521 (1998).
Uflacker, R., "Atlas of vascular anatomy: An angiographic approach." Baltimore: Williams & Wilkins, 424 (1997).
Valente, J. F. "Laparoscopic renal denervation for intractable ADPKD-related pain," Nephrol Dial Transplant, 16:160 (2001).
Van Hare, G. F., et al. "Percutaneous radiofrequency catheter ablation for supraventricular arrhythmias in children." JACC, 17:1613-1620 (1991).
Van Hare, George F., "Radiofrequency Catheter Ablation of Supraventricular Arrhythmias in Patients With Congenital Heart Disease: Results and Technical Considerations," J. of the Amer. College of Cardiol. 22(3):883-90, 1993.
Volkmer, Marius, M.D., "Focal Atrial Tachycardia from Deep Inside the Pulmonary Veins," PACE vol. 20:533, p. 1183 (1997).
Vujaskovie, Z., et al. "Effects of intraoperative hyperthermia on canine sciatic nerve: Histopathology and morphometric studies." Int. J. Hyperthermia, 10,6:845-855 (1994).
Walsh, Edward P., M.D., "Transcatheter Ablation of Ectopic Atrial Tachycardia in Young Patients Using Radiofrequency Current," Circulation, 86(4):1138-1146 (1992).
Wang, S., et al., Effects of Low Intensity Ultrasound on the Conduction Property of Neural Tissues, IEEE International Ultrasonics, Ferroelectrics, and Frequency Control, Joint 50th Anniversary Conference, 2004.
Weinstock, M., et al. "Renal denervation prevents sodium retention and hypertension in salt sensitive rabbits with genetic baroreflex impairment," Clinical Science, 90:287-293 (1996).
Weir, M. R., et al. "The renin-angiotensin-aldosterone system: A specific target for hypertension management." Am J Hypertens, 12:205S-213S (1999).
Written Opinion of the International Searching Authority for PCT/US2010/020333, dated Feb. 25, 2010, 7 pages.
Written Opinion dated Jul. 9, 2014 in Int'l PCT Patent Appl. Serial No. PCT/US2014/22804.
www.dictionary.com/browse/degrease, retrieved Jun. 7, 2016.
Yamamoto, T., et al. "Blood velocity profiles in the human renal artery by Doppler ultrasound and their relationship to atherosclerosis." Arterisocl Throm Vas, 16: 172-177 (1996).
Zhang et al., "The development of a RF electrical pole catheter for heart ablation," China Academic Journal Electronic Publishing House 23(5): 279-80, Sep. 1999 (With English Abstract).
Zipes, Douglas P., M.D., "Catheter Ablation of Arrhythmias," 1994.

(56) References Cited

OTHER PUBLICATIONS

Ahmed, Humera et al., Renal Sympathetic Denervation Using an Irrigated Radiofrequency Ablation Catheter for the Management of Drug-Resistant Hypertension, JACC Cardiovascular Interventions, vol. 5, No. 7, 758-765 (2012).
American Heart Association—Pulmonary Hypertension: High Blood Pressure in the Heart-to-Lung System, (last reviewed Oct. 31, 2016).
Bisdas, Theodosios et al., Initial Experience with the 6-F and 8-F Indigo Thrombectomy System for Acute Renovisceral Occlusive Events, Journal of Endovascular Therapy, vol. 24, No. 4, 604-610 (2017).
Blanketjin, Peter, Sympathetic Hyperactivity in Chronic Kidney Disease, Neprhrol Dial Transplant, vol. 19, No. 6, 1354-1357 (2004).
Bradfield, Jason S. et al., Renal denervation as adjunctive therapy to cardiac sympathetic denervation for ablation refractory ventricular tachycardia, Heart Rhythm Society, vol. 17, No. 2, 220-227 (2020).
Camasao, D.B. et al., The mechanical characterization of blood vessels and their substitutes in the continuous quest for physiological-relevant performances: A critical review, Materials Today Bio, vol. 10 (2021).
Carter, Stefan et al., Measurement of Renal Artery Pressures by Catheterization in Patients with and without Renal Artery Stenosis, Circulation, vol. XXXIII, 443-449 (1966).
Charlesworth, Peter et al., Renal Artery Injury From a Fogarty Balloon Catheter, Journal of Vascular Surgery, vol. 1, No. 4, 573-576 (1984).
Defendant's Reply to Court Order of Oct. 4, 2022 and Plaintiff's Surrejoinder of Sep. 29, 2022 in the Mannheim District Court, case No. 7 O 14/21, dated Oct. 31, 2022.
Plaintiff's Nullity Brief, dated Jan. 14, 2022, in the Munich Federal Patent Court, Nullity Suit 6 Ni 32/22.
Defendant's Response dated May 11, 2022 in the Munich Federal Patent Court, Nullity Suit 6 Ni 32/22.
Plaintiff's Reply to the May 11, 2022 Response, dated Jul. 18, 2022, in the Munich Federal Patent Court, Nullity Suit 6 Ni 32/22.
Plaintiff's Response to Court Order disagreeing with Stay of Proceedings dated Oct. 28, 2022 in Mannheim District Court, Infringement suit 7 O 147/21.
Plaintiff's Technical Brief dated Sep. 29, 2022 in the Mannheim District Court, Infringement suit 7 O 147/21.
Curriculum Vitae of Dr. John M. Moriarty.
Curriculum Vitae of Dr. Michael Bohm.
Deardorff, Dana et al., Ultrasound Applicators with Internal Water-Cooling for High-Powered Interstitial Thermal Therapy, IEEE Transactions on Biomedical Engineering, vol. 47, No. 10, 1356-1365 (2000).
Declaration of Dr. Dieter Haemmerich, dated Aug. 29, 2012, in the Patent Trial and Appeal Board, United States Patent and Trademark Office, In re U.S. Pat. No. 7,717,948.
Declaration of Dr. John M. Moriarty in German Nullity proceedings for EP 2261905, dated Jul. 13, 2022.
Declaration of Dr. Michael Bohm dated Sep. 29, 2022 on behalf of Medtronic Inc.
Dibona, Gerald, Sympathetic Nervous System and Kidney in Hypertension, Current Opinion in Nephrology and Hypertension, vol. 11, 197-200 (2002).
Draney, Mary et al., Three-Dimensional Analysis of Renal Artery Bending Motion During Respiration, International Society of Endovascular Specialists, vol. 12, 380-386 (2005).
EP Board of Appeals Communication dated Dec. 17, 2019— Preliminary Remarks for EP appeal No. T2680/16-3.3.4.01.
EP Communication dated Oct. 23, 2013 in EP Application No. 12180431.4.
EP Office Action re Application No. 12180431.4.
Erikson, Kenneth et al., Ultrasound in Medicine: A Review, IEEE Transactions on Sonics and Ultrasonics, vol. 21, No. 3 (1974).
European Search Report for Patent Application No. EP12180431 dated Jan. 17, 2013.
Gallitto, Enrico et al., Renal Artery Orientation Influences the Renal Outcome in Endovascular Thoraco-abdominal Aortic Aneurysm Repair, European Society of Endovascular Surgery, vol. 56, No. 3, 382-390 (2018).
Gray, Henry, Gray's Anatomy: The Anatomical Basis of Medicine and Surgery, Churchill Livingstone, New York, NY (1995).
Habict, Antje et al., Sympathetic Overactivity and Kidneys, The Middle European Journal of Medicine, vol. 115, 634-640 (2003).
He, D. S. et al., Application of Ultrasound Energy for Intracardiac Ablation of Arrhythmias, European Heart Journal, vol. 16, 961-966 (1995).
Janzen, Nicolette et al., Minimally Invasive Ablative Approaches in the Treatment of Renal Cell Carcinoma, Current Urology Reports, vol. 3 (2002).
Kaltenbach, Benjamin et al., Renal Artery Stenosis After Renal Sympathetic Denervation, Journal of the American College of Cardiology, vol. 60, No. 25 (2012).
Kim, Yun-Hyeon et al., Pulmonary vein diameter, cross-sectional area, and shape: CT analysis, Radiology Society of North America, vol. 235, No. 1, 49-50 (2005).
Kirsh, Danielle, Balloon Catheters: What are some key design considerations?, MASSDEVICE (Dec. 6, 2016).
Koomans, Hein et al., Sympathetic Hyperactivity in Chronic Renal Failure: A wake-up call, Frontiers in Nephrology, vol. 15, 524-537 (2004).
Lang, Roberto et al., Recommendations for Chamber Quantification: A Report from the American Society of Echocardiography's Guidelines and Standards Committee and the Chamber Quantification Writing Group, Developed in Conjunction with the European Association of Echocardiography, a Branch of the European Society of Cardiology, Journal of the American Society of Echocardiography, vol. 18, No. 12, 1440-1463 (2005).
Mahfoud, Felix et al., Catheter-Based Renal Denervation Is No Simple Matter: Lessons to Be Learned From Our Anatomy?, Journal of the American College of Cardiology, vol. 64, No. 7, 644-647 (2014).
Martin, Louis K. et al., Long-term Results of Angioplasty in 110 Patients with Renal Artery Stenosis, Journal of Vascular and Interventional Radiology, vol. 3, No. 4, 619-626 (1992).
Medtronic Inc., Renal Denervation (RDN): Novel Catheter-Based Treatment for Hypertension, Scientific Background, 2011.
Medtronic Inc., The Symplicity RDN System, 2012.
Meyers, Philip et al., Temporary Endovascular Balloon Occlusion of the Internal Carotid Artery with a Nondetachable Silicone Balloon Catheter: Analysis Technique and Cost, American Journal of Neuroradiology, vol. 20, No. 4, 559-564 (1999).
Natale, Andrea et al., First Human Experience with Pulmonary Vein Isolation Using a Through-the-Balloon Circumferential Ultrasound Ablation System for Recurrent Atrial Fibrillation, Circulation, vol. 102, 1879-1882 (2000).
Netter, Frank, Atlas of Human Anatomy, Icon Learning Systems, Rochester, NY (2002).
Neumann, Jutta, Sympathetic hyperactivity in chronic kidney disease: Pathogenesis, clinical relevance, and treatment, International Society of Nephrology, vol. 65, 1568-1576 (2004).
Prochnau, Dirk et al., Catheter-based renal denervation for drug-resistant hypertension by using a standard electrophysiology catheter, EuroIntervention, vol. 7, 1077-1080 (2012).
Ryan, Steve, What are the Risks Associated with a Pulmonary Vein Ablation Procedure?, Atrial Fibrillation: Resources for Patients (last accessed Oct. 18, 2022).
Ryan, Thomas et al., Proceedings of Thermal Treatment of Tissue with Image Guidance, Progress in Biomedical Optics, vol. 3594 (1999).
Sakakura, Kenichi et al., Anatomic Assessment of Sympathetic Peri-Arterial Renal Nerves in Man, Journal of the American College of Cardiology, vol. 64, No. 7, 635-643 (2014).
Schneider, Peter, Endovascular Skills: Guidewire and Catheter Skills for Endovascular Surgery, 2nd ed., Marcel Dekker, Inc., New York, NY (2003).
Shimizu, Kazumasa et al., Sympathetic Dysfunction in Heart Failure, Bailliere's Clinical Endocrinology and Metabolism, vol. 7, No. 2 (1993).

(56) References Cited

OTHER PUBLICATIONS

Slide deck from Medtronic Circulatory System Devices Panel Meeting, General Issues Panel: Clinical Evaluation of Anti-Hyperintensive Devices (Dec. 5, 2018).
Vaezy, Shahram et al., Image-Guided Acoustic Therapy, Annual Review Biomedical Engineering, vol. 3, 375-390 (2001).
Wanchoo, Nishey, Medtronic Gets European and Australian Approval for Symplicity Spyral Multi-Electrode Renal Denervation Catheter, Medgadget (2013).
Appeal Brief of Patent Owner from Reexamination 95-002, 110.
Correspondence from PTAB Deputy Chief Clerk to Counsel re conference call request—Exhibit 3001 in the Patent Trial and Appeal Board, United States Patent and Trademark Office, Petition No. PTAB-IPR2022-00431.
Corrected Patent Owner's Response to Office Action, dated May 10, 2013, from File History of Inter Partes Reexamination 95/002,110.
Chart showing priority claims of the '629 patent, exhibit to Petition for Inter Partes Review of U.S. Pat. No. 8,845,629, filed Jan. 13, 2022 in the Patent Trial and Appeal Board, United States Patent and Trademark Office, Petition No. PTAB-IPR2022-00431.
Curriculum Vitae of Dr. Chris Daft.
Curriculum Vitae of Dr. John M. Moriarty, M.D.
Curriculum Vitae of Farrell Mendelsohn.
Decision of the Patent Trial and Appeal Board in U.S. Appl. No. 14/731,347.
Declaration of Chris Daft dated Jan. 11, 2022, in the Patent Trial and Appeal Board, United States Patent and Trademark Office, Petition No. PTAB-IPR2022-00431.
Second Declaration of Dr. Chris Daft. Dated Jan. 10, 2023, in the Patent Trial and Appeal Board, United States Patent and Trademark Office, Petition No. PTAB-IPR2022-00431.
Declaration of Dr. Farrell Mendelsohn dated Jan. 10, 2022, in the Patent Trial and Appeal Board, United States Patent and Trademark Office, Petition No. PTAB-IPR2022-00431.
Declaration of Dr. Robert Tucker, dated Oct. 27, 2022, in the Patent Trial and Appeal Board, United States Patent and Trademark Office, Petition No. PTAB-IPR2022-00431.
Declaration of Dr. Daniel van der Weide, dated Oct. 26, 2022, in the Patent Trial and Appeal Board, United States Patent and Trademark Office, Petition No. PTAB-IPR2022-00431.
Declaration of Dr. John Moriarty, dated Jan. 19, 2023, in the Patent Trial and Appeal Board, United States Patent and Trademark Office, Petition No. PTAB-IPR2022-00431.
Declaration of Jonathan Bradford in Support of Patent Owner'sResponse.
Declaration of Jonathan Bradford dated May 10, 2022, in the Patent Trial and Appeal Board, United States Patent and Trademark Office, Petition No. PTAB-IPR2022-00431.
U.S. Appl. No. 10/408,665.
U.S. Appl. No. 60/624,793.
U.S. Appl. No. 60/370,190.
U.S. Appl. No. 60/415,575.
U.S. Appl. No. 60/442,970.
U.S. Appl. No. 60/616,254.
File History of U.S. Appl. No. 12/754,337, part 1, pp. 1-415.
File History of U.S. Appl. No. 12/754,337, part 2, pp. 416-789.
File History to U.S. Pat. No. 9,943,666.
File History to U.S. Pat. No. 9,981,108 Part 1.
File History to U.S. Pat. No. 9,981,108 Part 2.
File History to U.S. Pat. No. 10,039,901 Part 1.
File History to U.S. Pat. No. 10,039,901 Part 2.
File History to EP1802370B1 Part 1.
File History to EP1802370B1 Part 2.
File History to EP1802370B1 Part 3.
Institution Decision Granting Institution of Inter Partes Review 35 U.S.C. sec. 314, dated Aug. 8, 2022 in the Patent Trial and Appeal Board, United States Patent and Trademark Office, Petition No. PTAB-IPR2022-00431.
Notice of Deposition of Tucker, filed Dec. 30, 2022 in the Patent Trial and Appeal Board, United States Patent and Trademark Office, Petition No. PTAB-IPR2022-00431.
Notice of Deposition of van der Weide, filed Dec. 30, 2022 in the Patent Trial and Appeal Board, United States Patent and Trademark Office, Petition No. PTAB-IPR2022-00431.
Order: Conduct of the Proceeding Scheduling Order 37 C.F.R. sec. 42.5, dated Aug. 8, 2022 in the Patent Trial and Appeal Board, United States Patent and Trademark Office, Petition No. PTAB-IPR2022-00431.
Patent Owner's Amended Objections to Evidence Under 37 C.F.R. §42.64.
Patent Owner's Power of Attorney, filed Feb. 3, 2022 in the Patent Trial and Appeal Board, United States Patent and Trademark Office, Petition No. PTAB-IPR2022-00431.
Patent Owner's Mandatory Notice, filed Feb. 3, 2022 in the Patent Trial and Appeal Board, United States Patent and Trademark Office, Petition No. PTAB-IPR2022-00431.
Notice re filing date accorded, dated Feb. 10, 2022 in the Patent Trial and Appeal Board, United States Patent and Trademark Office, Petition No. PTAB-IPR2022-00431.
Patent Owner's Updated Mandatory Notice, filed May 10, 2022 in the Patent Trial and Appeal Board, United States Patent and Trademark Office, Petition No. PTAB-IPR2022-00431.
Patent Owner Medtronic Ireland Power of Attorney, filed May 10, 2022 in the Patent Trial and Appeal Board, United States Patent and Trademark Office, Petition No. PTAB-IPR2022-00431.
Patent Owner's Preliminary Response, filed May 10, 2022 in the Patent Trial and Appeal Board, United States Patent and Trademark Office, Petition No. PTAB-IPR2022-00431.
Patent Owner's Objections to Evidence, filed Aug. 18, 2022 in the Patent Trial and Appeal Board, United States Patent and Trademark Office, Petition No. PTAB-IPR2022-00431.
Patent Owner's Notice of Deposition of Dr. Chris Daft, filed Sep. 20, 2022 in the Patent Trial and Appeal Board, United States Patent and Trademark Office, Petition No. PTAB-IPR2022-00431.
Patent Owner's Notice of Deposition of Dr. Farrell Mendelsohn, filed Sep. 21, 2022 in the Patent Trial and Appeal Board, United States Patent and Trademark Office, Petition No. PTAB-IPR2022-00431.
Patent Owner's Response, filed Oct. 27, 2022 in the Patent Trial and Appeal Board, United States Patent and Trademark Office, Petition No. PTAB-IPR2022-00431.
Patent Owner's Notice of Deposition of Dr. Chris Daft filed Feb. 21, 2023 in the Patent Trial and Appeal Board, United States Patent and Trademark Office, Petition No. PTAB-IPR2022-00431.
Patent Owner's Notice of Deposition of Dr. John Moriarty, filed Feb. 21, 2023 in the Patent Trial and Appeal Board, United States Patent and Trademark Office, Petition No. PTAB-IPR2022-00431.
Patent Owner's Sur-Reply, filed Mar. 9, 2023 in the Patent Trial and Appeal Board, United States Patent and Trademark Office, Petition No. PTAB-IPR2022-00431.
Patent Owner's Request for Oral Hearing, filed Mar. 23, 2023 in the Patent Trial and Appeal Board, United States Patent and Trademark Office, Petition No. PTAB-IPR2022-00431.
Petition for Inter Partes Review of U.S. Pat. No. 8,845,629, dated Jan. 13, 2022 by ReCor Medical, Inc. and Otsuka Medical Devices Co., Ltd., in the Patent Trial and Appeal Board, United States Patent and Trademark Office, Petition No. PTAB-IPR2022-00431.
Petitioners' Updated Mandatory Notices, dated Jan. 18, 2022 in the Patent Trial and Appeal Board, United States Patent and Trademark Office, Petition No. PTAB-IPR2022-00431.
Petitioner Reply, filed Jan. 23, 2023 in the Patent Trial and Appeal Board, United States Patent and Trademark Office, Petition No. PTAB-IPR2022-00431.
Petitioners' Request for Oral Argument, filed Mar. 21, 2023 in the Patent Trial and Appeal Board, United States Patent and Trademark Office, Petition No. PTAB-IPR2022-00431.
Petitioner ReCor's Biography of Dr. Neil C. Barman.
Power of Attorney for Otsuka Medical Devices Co., Ltd., filed Jan. 13, 2022 in the Patent Trial and Appeal Board, United States Patent and Trademark Office, Petition No. PTAB-IPR2022-00431.

(56) References Cited

OTHER PUBLICATIONS

Power of Attorney for Recor Medical, Inc., filed Jan. 13, 2022 in the Patent Trial and Appeal Board, United States Patent and Trademark Office, Petition No. PTAB-IPR2022-00431.
Setting Oral Hearing 37 C.F.R. § 42.70, dated Mar. 24, 2023 in the Patent Trial and Appeal Board, United States Patent and Trademark Office, Petition No. PTAB-IPR2022-00431.
Schedule Stipulation, dated Dec. 30, 2022 in the Patent Trial and Appeal Board, United States Patent and Trademark Office, Petition No. PTAB-IPR2022-00431.
Selected documents from the File History of Inter Partes Reexamination 95/002110, exhibit to Petition for Inter Partes Review of U.S. Pat. No. 8,845,629, filed Jan. 13, 2022 in the Patent Trial and Appeal Board, United States Patent and Trademark Office, Petition No. PTAB-IPR2022-00431.
Stipulation Modifying Schedule, dated Feb. 16, 2023 in the Patent Trial and Appeal Board, United States Patent and Trademark Office, Petition No. PTAB-IPR2022-00431.
Transcript of the Sep. 30, 2022 deposition of Dr. Chris Daft.
Transcript of the Oct. 1, 2022 deposition of Dr. Farrell Mendelsohn.
Transcript of the Mar. 3, 2023 deposition of Dr. Chris Daft.
Transcript of the Mar. 2, 2023 deposition of Dr. John Moriarty.
Transcript of deposition of the Jan. 1, 2023 deposition of Dr. Robert Tucker.
Transcript of the Jan. 14, 2023 deposition of Dr. Daniel van der Weide.
Aytac, et al., "Correlation Between the Diameter of the Main Renal Artery and the Presence of an Accessory Renal Artery", J Ultrasound Med 22:433-439, 2003 (.
Azizi, Michel et al., Ultrasound renal denervation for hypertension resistant to a triple medication pill (RADIANCE-HTN TRIO): a randomised, multicentre, single-blind, sham-controlled trial, 397 Lancet 2476 (2021).
Bailey, M.R. et al., Physical Mechanisms of the Therapeutic Effect of Ultrasound (A Review), Acoustical Physics, vol. 49, No. 4, 2003, pp. 369-388.
Bengel, et al., Serial Assessment of Sympathetic Reinnervation After Orthotopic Heart Transplantation; A Longitudinal Study Using PET and C-11 Hydroxyephedrine, Circulation. 1999;99: 1866-1871.
Bhatt, Deepak L. et al., Long-term outcomes after catheter-based renal artery denervation for resistant hypertension: final follow-up of the randomised SYMPLICITY HTN-3 Trial, 400 Lancet 1405 (2022).
Blum et al., Treatment of Ostial Renal-Artery Stenoses with Vascular Endoprostheses after Unsuccessful Balloon Angioplasty, N. Engl. J. Med. 336 459-65 (1997).
Bonsignore, C., "A Decade of Evolution in Stent Design", Proceedings of the International Conference on Shape Memory and Superelastic Technologies, (2003).
Bradfield, J.S., et al., "Renal denervation as adjunctive therapy to cardiac sympathetic denervation for ablation refractory ventricular tachycardia.", Heart Rhythm. Feb. 2020;17(2):220-22)(2020).
Bush, et al., "Endovascular revascularization of renal artery stenosis: Technical and clinical results", Journal of Vascular Surgery, May 2001, 1041-1049 (2001).
Chiesa et al., Endovascular Stenting for the Nutcracker Phenomenon, J. Endovasc. Ther., 8:652-655 (2001).
Dangas, G., et al., Intravascular Ultrasound-Guided Renal Artery Stenting, J Endovasc Ther, 2001;8:238-247 (2001).
Diederich, et al., Ultrasound Catheters For Circumferential Cardiac Ablation, in Proceedings of SPIE Conference on Thermal Treatment of Tissue with Image Guidance San Jose, California, Jan. 1999 SPIE vol. 3594.
Fengler, Karl et al., A Three-Arm Randomized Trial of Different Renal Denervation Devices and Techniques in Patients With Resistant Hypertension (RADIOSOUND-HTN), 139 Circulation 590 (2019).
Gervais, Debra A. et al., Radiofrequency ablation of renal cell carcinoma: Part 2, Lessons learned with ablation of 100 tumors, 185 AJR Am. J. Roentgenol. 72 (2005).

Goldberg, S. Nahum et al., EUS-guided radiofrequency ablation in the pancreas: results in a porcine model, 50 Gastrointest. Endosc. 392 (1999).
Golwyn et al., Percutaneous Transcatheter Renal Ablation with Absolute Ethanol for Uncontrolled Hypertension or Nephrotic Syndrome: Results in 11 Patients with End-Stage Renal Disease, J. Vasco and Interventional Radiology, 8,527-433 (1997).
Hansen et al., The Transplanted Human Kidney Does Not Achieve Functional Reinnervation, 87 Clinical Science 13 (1994).
Holmes, David R. et al., Pulmonary vein stenosis complicating ablation for atrial fibrillation: clinical spectrum and interventional considerations, 2 JACC Cardiovasc. Interv. 267 (2009).
Hsu, Thomas H. S. et al., Radiofrequency ablation of the kidney: acute and chronic histology in porcine model, 56 Urology 872 (2000).
Huang, et al., Renal Denervation Prevents and Reverses Hyperinsulinemia-Induced Hypertension in Rats, Hypertension 32 (1998) pp. 249-254.
Isles et al., Management of Renovascular Disease: A Review of Renal Artery Stenting in Ten Studies, QJM 92, 159-67 (1999).
Kapural, Leonardo, et al., "Radiofrequency Ablation for Chronic Pain Control," Anesthetic Techniques in Pain Management, pp. 517-525, 2001.
Katholi, R.E., et. al., Importance of Renal Sympathetic Tone in the Development of DOCA-Salt Hypertension in The Rat, Hypertension, 2:266-273 (1980).
Kuo, et al., "Atrial Fibrillation: New Horizons", Chang Gung Med J vol. 26 No. 10 Oct. 2003.
Lee, Jong Deok et al., MR imaging-histopathologic correlation of radiofrequency thermal ablation lesion in a rabbit liver model: observation during acute and chronic stages, 2 Korean J. Radiol. 151 (2001).
Levin, S., et al., ARDIAN: Succeeding Where Drugs Fail—Treating Hypertension in the Cath Lab, In Vivo, 27:23 (2009).
Marine, Joseph E., Catheter ablation therapy for supraventricular arrhythmias, 298 JAMA 2768 (2007).
Matsumoto, Edward D. et al., Short-term efficacy of temperature-based radiofrequency ablation of small renal tumors, 65 Urology 877 (2005).
Medtronic Scientific Background, Hypertension and the Symplicity Renal Denervation System.
Medtronic, Symplicity RDN Common System Q&A.
Millard, et al., Renal Embolization For Ablation of Function In Renal Failure And Hypertension, Postgraduate Med. J. 65, 729-734 (1989).
Natale, et al. "First Human Experience With Pulmonary Vein Isolation Using a Through-the-Balloon Circumferential Ultrasound Ablation System for Recurrent Atrial Fibrillation", Circulation, (2000) 102:1879-1882.
News, Columbia University Irving Medical Center, Zapping Nerves with Ultrasound Lowers Drug-Resistant Blood Pressure (May 16, 2021), https://www.cuimc.columbia.edu/news/zapping-nervesultrasound-lowers-drug-resistant-blood-pressure.
Page, Irvine H. & George J. Heuer, The Effect of Renal Denervation on Patients Suffering from Nephritis, 14 J. Clinical Investigation 443 (1935) (received for publication in 1935).
Papademetriou, Vasilios et al., Renal Sympathetic Denervation for the Treatment of Difficult-to-Control or Resistant Hypertension, 2011 Int. J. Hypertension, Article 196518 (2011).
Pappone C, et al., "Circumferential radiofrequency ablation of pulmonary vein ostia: a new anatomic approach for curing atrial fibrillation", Circulation. 2000; 102(21): 2619-2628. (2000).
Plouin et al., Blood Pressure Outcome of Angioplasty in Atherosclerotic Renal Artery Stenosis: A Randomized Trial. Essai Multicentrique Medicaments vs Angioplastie (EMMA) Study Group, Hypertension 31, 823-29 (1998).
Purerfellner, Helmut et al., Incidence, Management and Outcome in Significant Pulmonary Vein Stenosis Complicating Ablation for Atrial Fibrillation, 93 Am. J. Cardiol. 1428 (2004).
Purerfellner, Helmut & Martin Martinek, Pulmonary vein stenosis following catheter ablation of atrial fibrillation, 20 Curr. Opin. Cardiol. 484 (2005).

(56) References Cited

OTHER PUBLICATIONS

Romanes, G.J., Cunningham's Textbook of Anatomy (11th ed. 1972).
Sánchez-Quintana, Damian et al., How close are the phrenic nerves to cardiac structures? Implications for cardiac interventionalists, 16 J. Cardiovasc. Electrophysiol 309 (2005) ("Sánchez-Quintana").
Schneider, Peter A., Endovascular Skills, Quality Medical Publishing, Inc., 1998 ("Schneider").
Schmieder, Ronald E., Renal denervation in patients with chronic kidney disease: current evidence and future perspectives, Nephrol. Dial. Transplant. gfac189 (2022).
Shonai et al., Renal Artery Aneurysm: Evaluation with Color Doppler Ultrasonography Before and lifter Percutaneous Transarterial Embolization, J. Ultrasound Med. 19, 277-80 (2000)("Shonai 2000").
Smithwick, R. H., et al., "Splanchnicectomy for essential hypertension." J. Am. Med. Assoc., 152:1501-1504 (1953).
Stoeckel, D. et al., A Survey of Stent Designs, Min Invas Ther & Allied Technol 2002: 11(4) 137-147 (2002).
Teigen et al., Segmental Renal Artery Embolization for Treatment of Pediatric Renovascular Hypertension, J. Vasco Interv. Radiol. 3, 111-7 (1992).
Thatipelli, Mallik R., et al., CT angiography of renal artery anatomy for evaluating embolic protection devices, 18 J. Vasc. Interv. Radiol. 842 (2007).
The Doctors and Experts at WebMD, Webster's New World Medical Dictionary (3rd ed. 2008) ("WebsterMD").
Tsao, Hsuan-Ming et al., Evaluation of Pulmonary Vein Stenosis after Catheter Ablation of Atrial Fibrillation, 6 Card. Electrophysiol. Rev. 397 (2002).
Turner, et al., "Initial Experience Using the Palmaz Corinthian Stent for Right Ventricular Outflow Obstruction in Infants and Small Children", Catheterization and Cardiovascular Interventions 51:444-449 (2000).
Zazgornik, "Bilateral Nephrectomy: The best, but often overlooked, treatment for refractory hypertension in hemodialysis patients," Am. J. Hypertension, 11:1364-1370 (1998).
Ziegler et al., Sources of Urinary Catecholamines in Renal Denervated Transplant Recipients, 8 J. Hypertension No. 10, 927 (1990).
Coates, Paul et al., "Time, Temperature, Power, and Impedance Considerations for Radiofrequency Catheter Renal Denervation," Cardiovascular Revascularization Medicine 42, 171-177 (2022).
Sato, Yu, et al., "Translational Value of Preclinical Models for Renal Denervation: a histological comparison of human versus porcine renal nerve anatomy," EuroIntervention, 18, e1120-e1128, 2023.
Ahmed, Muneeb et al., "Thermal Ablation Therapy for Hepatocellular Carcinoma," J. Vasc. Interv, Radiol., vol. 13, No. 9 pt. 2, 2002.
Benito, Fernando et al., "Radiofrequency catheter ablation of accessary pathways in infants," Heart, vol. 78, p. 160-162, 1997.
Chang, Isaac A. et al., "Thermal Modeling of Lesion Growth with Radiofrequency Ablation Devices," Biomedical Engineering Online vol. 3, p. 27, 2004.
Chung, Andrew et al., "Thermal dosimetry of a focused ultrasound beam in vivo by magnetic resonance imaging," Medical Physics, vol. 26, No. 9, p. 2017-2026, Sep. 1999.
Damianou, Christakis et al., "High Intensity Focused Ultrasound Ablation of Kidney Guided MRI," Ultrasound in Med. & Biol., vol. 30, No. 3, p. 397-404, 2004.
Deardorff, Dana L. et al., "Axial Control of Thermal Coagulation Using a Multi-Element Interstitial Ultrasound Applicator with Internal Cooling," IEE Transactions on Ultrasonics, Ferroelectrics, and Frequency Control, vol. 47, No. 1, p. 170-178, Jan. 2000.
Dewhirst, M.W. et al., "Basic Principles of Thermal Dosimetry and Thermal Thresholds for Tissue Damage from Hyperthermia," International Journal of Hyperthermia vol. 19, No. 3, p. 267-294, May-Jun. 2003.
Diederich, Chris J. et al., "Ultrasound Technology for Hyperthermia," Ultrasound in Med. & Biol., vol. 25, No. 6, p. 871-887, 1999.

Fry, F.J. et al., "Production of Reversible Changes in the Central Nervous System by Ultrasound," Science, vol. 127, p. 83-84, Jan. 1958.
Gavrilov, L.R. et al., The Effect of Focused Ultrasound on the Skin and Deep Nerve Structures of Man and Animal, p. 279-292.
Gavrilov, L.R., "Use of Focused Ultrasound for Stimulation of Nerve Structures," Ultrasonics, p. 132-138, May 1984.
Graham, S.J. et al., "Quantifying Tissue Damage Due to Focused Ultrasound Heating Observed by MRI" Magnetic Resonance in Medicine vol. 41, p. 321-328, 1999.
Goldberg, S. Nahum et al., "Radiofrequency Tissue Ablation: Increased Lesion Diameter with a Perfusion Electrode," Acad. Radiol. vol. 3, No. 8, p. 636-644, Aug. 1996.
Häcker, Axel et al., "Extracorporeal Organotripsy for Renal Tumours," Current Opinion in Urology, vol. 13, p. 221-225, 2003.
Hausberg, Martin et al., "Sympathetic Nerve Activity in End-Stage Renal Disease," Circulation, vol. 106, p. 1974-1979, 2002.
Ho, Siew Yen et al., "Anatomy of the Left Atrium: Implications for Radiofrequency Ablation of Atrial Fibrillation," J Cardiovasc Electrophysiol., vol. 10, p. 1525-1533, Nov. 1999.
Israel, Gary M. et al., "MRI of the Kidney and Urinary Tract," Journal of Magnetic Resonance Imaging, vol. 24, p. 725-734, 2006.
Jiang, S.C. et al., "Effects of Thermal Properties and Geometrical Dimensions on Skin Burn Injuries," Burns, vol. 28, p. 713-717, 2002.
Kaye, David M. et al., "Functional and Neurochemical Evidence for Partial Cardiac Sympathetic Reinnervation After Cardiac Transplantation in Humans," Circulation, vol. 88, No. 3, Sep. 1993.
Keane, David, "New Catheter Ablation Techniques for the Treatment of Cardiac Arrhythmias," Cardiac Electrophysiology Review vol. 6, No. 4, p. 341-348, 2002.
Kennedy, J.E. et al., "High Intensity Focused Ultrasound: Surgery of the Future?", The British Journal of Radiology, vol. 76, p. 590-599, Sep. 2003.
Lai, Yu-Chi et al., "Lesion Size Estimator of Cardiac Radiofrequency Ablation at Different Common Locations with Different Tip Temperatures," IEEE Transactions on Biomedical Engineering vol. 51, No. 10, p. 1859-1864, Oct. 2004.
Lauder, Lucas et al., "Renal Denervation in the Management of Hypertension," EuroIntervention, vol. 20, p. e467-e478, 2024.
Lele, P.P., "Effects of Focused Ultrasonic Radiation on Peripheral Nerve, with Observations on Local Heating," Experimental Neurology, vol. 8, p. 47-83, 1963.
Liao, Qingyao et al., "Optimal Strategy for HIFU-Based Renal Sympathetic Denervation in Canines," Frontiers in Cardiovascular Medicine vol. 8, p. 1-11, Oct. 2021.
Liem, L. Bing, "Progress in Cardiac Arrhythmia Ablation: Potential for Broader Application and Shorter Procedure Time," Journal of Cardiothoracic and Vascular Anesthesia, vol. 11, No. 7, p. 895-900, Dec. 1997.
Lin, James C., "Physical Aspects of Radiofrequency Ablation," Radiofrequency Catheter Ablation of Cardiac Arrhythmias, Basical Concepts and Clinical Applications, Second Edition, Edited by Shoei K. Stephen Huang & David K. Wilber, 2000.
Mahfoud, Felix et al., "Device Therapy of Hypertension," Circulation Research nol. 128, p. 1080-1099, Apr. 2021.
Makin, Inder Raj. S. et al., "Miniaturized Ultrasound Arrays for Interstitial Ablation and Imaging," Ultrasound in Med. & Biol. vol. 31, No. 11, p. 1539-1550, 2005.
Malcolm, A.L. et al., "Ablation of Tissue Volumes Using High Intensity Focused Ultrasound" Ultrasound in Med. & Biol. vol. 22 No. 5 p. 659-669, 1996.
Manolis, Antonis S. et al., "Radiofrequency Catheter Ablation for Cardiac Tachyarrhythmias," Annals of Internal Medicine, vol. 131, No. 6, p. 452-461, Sep. 1994.
Mitchell, G.A.G et al., "An Anatomical Evaluation of Operations for Hypertension," Proceedings of the Anatomical Society vol. LIV., No. 10, p. 545-560.
Mompeo, Blanca et al., "The Gross Anatomy of the Renal Sympathetic Nerves Revisited," Clinical Anatomy vol. 29, p. 660-664, Apr. 2016.

(56) References Cited

OTHER PUBLICATIONS

Moore, J.H. et al., "The Biophysical Effects of Ultrasound on Median Nerve Distal Latencies," Electromyogr. Clin. Neurophysiol., vol. 40, p. 169-190, 2000.
Nath, Sunil et al., "Basic Aspects of Radiofrequency Catheter Ablation," Journal of Cardiovascular Electrophysiology vol. 5, No. 10, p. 863-876, Oct. 1994.
Nath, Sunil et al., "Biophysics and Pathology of Catheter Energy Delivery Systems," Progress in Cardiovascular Diseases, vol. XXXVII, No. 4, p. 185-204, Jan./Feb. 1995.
Nau, William H. et al., "MRI-Guided Interstitial Ultrasound Thermal Therapy of the Prostate: A Feasibility Study in the Canine Model," Medical Physics vol. 32, No. 3, p. 733-743, Mar. 2005.
Nikfarjam, Mehrdad et al., "Mechanisms of Focal Heat Destruction of Liver Tumors," Journal of Surgical Research, vol. 127, No. 2, p. 208-223, Aug. 2005.
Ninet, Jean et al., "Surgical Ablation of Atrial Fibrillation With Off-Pump, Epicardial, High-Intensity Focused Ultrasound: Results of A Multicenter Trial," The Journal of Thoracic and Cardiovascular Surgery, vol. 130, No. 3, p. 803.e1-803 e.8, Sep. 2005.
Ohkubo, Toyoyuki et al., "Experimental Study of Catheter Ablation Using Ultrasound Energy in Canine and Porcine Hearts," Jpn. Heart J. vol. 39, No. 3, p. 399-409, May 1998.
Papademetriou, Vasilios et al., "Renal Nerve Ablation for Resistant Hypertension, How Did We Get Here, Present Status, and Future Directions," Circulation, No. 129, p. 1440-1451, 2014.
Pozzoli, Alberto et al., "Electrophysiological Efficacy of Epicor High-Intensity Focused Ultrasound," European Journal of Cardio-Thoracic surgery, vol. 42, p. 129-134, 2012.
Riis, Thomas et al., "Effective Ultrasonic Stimulation in Human Peripheral Nervous System," IEE Transactions on Biomedical Engineering, vol. XX, No. XX, p. 1-8, XXXX 2021.
Roux, N. et al., "The Myocardial Sleeves of the Pulmonary Veins: Potential Implications for Atrial Fibrillation," Surg. Radiol. Anat., vol. 26, p. 285-289, Feb. 2004.
Schuarte, Patrick et al., "Catheter Ablation of Cardiac Autonomic Nerves for Prevention of Vagal Atrial Fibrillation," Circulation vol. 102, p. 2774-2780, 2000.
Tellez, Armando et al., "Renal Artery Nerve Distribution and Density in the Porcine Model: Biologic Implications for the Development of Radiofrequency Ablation Therapies," Translational Research vol. 162 No. 6, p. 381-389, Dec. 2013.
Ter Haar, G., "Ultrasound Focal Beam Surgery," Ultrasound in Med. & Biol., vol. 21, No. 9, p. 1089-1100, 1995.
Ter Haar, G.R. et al., "Ultrasonic Heating of Mammalian Tissues In vivo," Br. J. Cancer vol. 45, Supp. V., p. 65-67, 1982.
Ter Haar, Gail R. "Therapeutic and Surgical Applications," Physical Principles of Medical Ultrasonics, Second Edition, Edited by C.R. Hill, J.C. Bamber, and G.R. Ter Haar, p. 407-456, 2004.
Trippodo, Nick C. et al., "Similarities of Genetic (Spontaneous) Hypertension," Circulation Research vol. 48, No. 3, p. 309-319, Mar. 1981.
Urban, Bruce A. et al., "Three-dimensional vol. rendered CT Angiography of the Renal Arteries and Veins: Normal Anatomy, Variants, and Clinical Applications," RG vol. 21 No. 2, p. 373-386, Mar.-Apr. 2001.
Wang, Shyh-Hau et al., "Effects of Low Intensity Ultrasound on the Conduction Property of Neural Tissues," IEEE International Ultrasonics, Ferroelectrics, and Frequency Control Joint $50^{th}$ Anniversary Conference, p. 1824-1827, 2004.
Weld, Kyle J. et al., "Comparison of Cryoablation, Radiofrequency Ablation and High-Intensity Focused Ultrasound for Treating Small Renal Tumours" BJU International vol. 96, p. 1224-1229, 2005.
Wells, P.N.T., "Functional Modification: Clinical Applications," Biomedical Ultrasonics, p. 470-504, 1977.
Winternitz, Sherry R. et al., "Importance of the Renal Nerves in the Pathogenesis of Experimental Hypertension," Hypertension (supp. III), vol. 4, No. 5, p. III-08-III-115, Sep.-Oct. 1982.
Wulff, V.J. et al., "Effects of Ultrasonic Vibrations on Nerve Tissues," P.S.E.B.M., vol. 76, p. 361-366, 1951.

Yarmolenko, Pavel S. et al., "Thresholds for thermal damage to normal tissues: An update," Int. J. Hyperthermia, vol. 27 No. 4, p. 320-343, Jun. 2011.
Young, Robert R. et al., "Functional Effects of Focused Ultrasound on Mammalian Nerves," Science, vol. 134, p. 1521-1522, Nov. 1961.
Zimmer, J.E. et al., "The Feasibility of Using Ultrasound for Cardiac Ablation," IEEE Transactions on Biomedical Engineering, vol. 42, No. 9, p. 891-897, Sep. 1995.
Accornero, Neri et al., "Selective Activation of Peripheral Nerve Fibre Groups of Different Diameter by Triangular Shaped Stimulus Pulses", J. Physiol. (1977), 273, 539-560, 22 Q9S.
Berjano, E., et al., "A Cooled Intraesophageal Balloon to Prevent Thermal Injury during Endocardial Surgical Radiofrequency Ablation of the left Atrium: a finite element study." Physics in Medicine and Biology, 50(20): 269-279, 2015.
Billard, B.E., et al., Effects of Physical Parameters on High Temperature Ultrasound Hyperthermia, Ultrasound in Med. & Biol. vol. 16, No. 4, pp. 409-420, 1990.
Carter, J., "Microneurography and Sympathetic Nerve Activity: A Decade-By-Decade Journey across 50 Years," Journal of Neurophysiology, vol. 121, No. 4. doi: 10.1 152/jn.00570.2018.
Chapelon, J.Y., "Treatment of Localised Prostate Cancer with Transrectal High Intensity Focused Ultrasound," European Journal of Ultrasound 9, 31-38, 1999.
Deardorff, Dana et al., Ultrasound Applicators with Internal Cooling for Interstitial Thermal Therapy, SPIE vol. 3594, 36-46, Jan. 1999.
Dibona, Gerald F., "Neural Control of the Kidney, Past, Present and Future," 41 [Part II] Hypertension 621 24 (2003).
Diederich, et al., "Catheter-based Ultrasound Applicators for Selective Thermal Ablation: progress towards MRI-guided applications in prostate," International Journal of Hyperthermia, 20:7, 739-756.
Diedrich, A. et al., "Analysis of Raw Microneurographic Recordings Based on Wavelet De-Noising Technique and 1 Classification Algorithm: Wavelet Analysis in Microneurography," IEEE Trans Biomed Eng. Jan. 2003 ; 50(1): 41-50_ doi:10.1109fTBME.2002. 807323.
European Patent No. 12167931, Claims of the Main Request dated Sep. 30, 2016.
European Search Report dated Mar. 1, 2021 in European Patent Application No. 20202272.9.
European Search Report dated Nov. 19, 2018 in European Patent Application No. 218186547.
Fan, Xiaobing, et al., "Control of the Necrosed Tissue Volume during Noninvasive Ultrasound Surgery using a 16-Element Phased Array," Department of Radiology, Brigham and Women's Hospital, Harvard Medical School, Oct. 31, 1994.
Foley, Jessica L., et al., "Image-Guided HIFU Neurolysis of Peripheral Nerves to Treat Spasticity and Pain," Ultrasound in Med & Biol., vol. 30, Np. 9 pp. 1199-1207, 2004.
Harrison, R.R. et al., "A Low-Power Integrated Circuit for a Wireless 1 OD-Electrode Neural Recording System," IEEE Journal of Solid-State Circuits, vol. 42, No. 1, pp. 123-133, Jan. 2007. doi: 10.1 109/JSSC.2006.886567.
Heffner, H. et al., "Gain, Band Width, and Noise Characteristics of the Variable-Parameter Amplifier," Journal of Applied Physics, vol. 29, No. 9, Sep. 1958, 1 1 pages.
Ivanisevic, N., "Circuit Design Techniques for Implantable Closed-Loop Neural Interfaces," Doctoral Thesis in Information and Communication Technology, KTH School of Electrical Engineering and Computer Science, Sweden, May 2019, 92 pages.
Janssen, B. J. A., et al. "Renal nerves in hypertension." Miner Electrolyte Metab., 15:74-82 (1989).
Kompanowska-Jezierska, Elzbieta et al., Early Effects of Renal Denervation in the Anaesthetized Rat: Natriuresis and Increased Cortical Blood Flow, 531 J. Physiology No. 2, 527 (2001).
Maslov, P., "Recruitment Pattern of Muscle Sympathetic Nerve Activity in Chronic Stable Heart Failure Patients and in Healthy Control Subjects," Doctoral Dissertation, University of Split, Croatia, 2013, 69 pages.
Nair et al., "The Need for and the Challenges of Measuring Renal Sympathetic Nerve Activity," Heart Rhythm 2016; 13:1166-1171.

(56) References Cited

OTHER PUBLICATIONS

Olsson, R. et al., "A Three-Dimensional Neural Recording Microsystem With Implantable Data Compression 5 Circuitry," ISSCC. 2005 IEEE International Digest of Technical Papers. Solid-State Circuits Conference, 2005., San Francisco, CA, 2005, pp. 558-559 vol. 1 doi:10.1109/JSSC.2005.858479.

Osborn, J., "Catheter-Based Renal Nerve Ablation as a Novel Hypertension Therapy, Lost, and Then Found," in Translation.

Papademetriou, et al., "Renal Sympathetic Denervation: Hibernation or Resurrection?", Cardiology 2016 ; 135, 11 pgs.

Papadopoulos, N., "Evaluation of a Small Flat Rectangular Therapeutic Ultrasonic Transducer Intended for Intravascular Use," Ultrasonics 74, 196-203, 2017.

Prakash, Punit, et al., "Considerations for Theoretical Modeling of Thermal Ablation with Catheter-Based Ultrasonic Sources: Implications for Treatment Planning, Monitoring and Control," International Journal of Hyperthermia, 28:1, 69-86.

Reaz, M.B.I., et al., "Techniques of EMG signal analysis: detection, processing, classification and applications," Biological Procedures Online, Jan. 2006, 25 pages.

Reddy, Vivek Y., "Use of a Diode Laser Balloon Ablation Catheter to Generate Circumferential Pulmonary Venous Lesions in an Open-Thoracotomy Caprine Model," PACE, vol. 27, 52-57, Jan. 2004.

Ryan, Thomas P._ Thermal Treatment of Tissue with Image Guidance; Ultrasound Catheters For Circumferential Cardiac Ablation 1999.

Salmanpour, A., L. J. Brown and J. K. Shoemaker, "Detection of Single Action Potential in Multi-Unit Postganglionic 7 Sympathetic Nerve Recordings in Humans: A Matched Wavelet Approach," 2010 IEEE International Conference on Acoustics, Speech and Signal Processing, Dallas, TX, 2010, pp. 554-557. doi: 10.1 109/ICASSP.2010.5495604.

Schlaich, M.P. et al., "Renal Denervation: A Potential New Treatment Modality for Polycystic Ovary Syndrome," Journal of Hypertension, vol. 29, No. 5, pp. 991-996 2011 . doi:10.1097/HJH.0b013e328344db3a.

Schmidt, Boris, et al., "Pulmonary Vein Isolation by High Intensity Focused Ultrasound," Indian Pacing and Electrophysiology Journal, pp. 126-133 (2006).

Tank, J. et al., "Spike Rate of Multi-Unit Muscle Sympathetic Nerve Fibers Following Catheter-Based Renal Nerve Ablation," J Am. Soc Hypertens, Oct. 2015 ; 9(10): 794-801 . doi:10.1016/j.jash.2015.07.012.

Ulmsten, Ulf et al., "The Safety and Efficacy of MenoTreat™, a new balloon device for thermal endometrial ablation," Acta Obstet Gynecol Scand 2001; 80: 52-57.

Xu, J. et al, "A Bidirectional Neuromodulation Technology for Nerve Recording and Stimulation, Micromachines," vol. 9, 1 1 538. Oct. 23, 2018. doi:10.3390/mi9110538.

Xu, J., T. Wu and Z. Yang, "A New System Architecture for Future Long-Term High-Density Neural Recording," IEEE Transactions on Circuits and Systems II: Express Briefs, vol. 60, No. 7, pp. 402-406, Jul. 2013. doi:10.1109/ TCSII.2013.2258270.

U.S. Appl. No. 17/453,636, filed Nov. 4, 2021.

U.S. Appl. No. 60/816,999.

U.S. Appl. No. 14/683,966, Non Final Office Action mailed Jun. 12, 2017, 14 pgs.

U.S. Appl. No. 14/683,966, Response filed Nov. 10, 2017 to Non Final Office Action mailed Jun. 12, 2017, 13 pqs.

U.S. Appl. No. 14/683,966, Notice of Allowance mailed Jan. 31, 2018, 8 pgs.

U.S. Appl. No. 14/683,966, PTO Response to Rule 312 Communication mailed Mar. 29, 2018, 2 pgs.

U.S. Appl. No. 14/683,966, 312 Amendment filed Mar. 13, 2018, 10 pgs.

U.S. Appl. No. 14/683,966, Corrected Notice of Allowance mailed May 22, 2018, 4 pgs.

U.S. Appl. No. 15/204,349, Preliminary Amendment filed Nov. 30, 2016, 3 pgs.

U.S. Appl. No. 15/204,349, Restriction Requirement mailed May 17, 2018, 7 pgs.

U.S. Appl. No. 15/204,349, Response filed Jun. 5, 2018 to Restriction Requirement mailed May 17, 2018, 7 pgs.

U.S. Appl. No. 60/747,137, File History.

U.S. Appl. No. 60/808,306, File History.

U.S. Appl. No. 61/405,472, File History.

U.S. Appl. No. 15/204,349, Non Final Office Action mailed Nov. 27, 2018, 14 pgs.

U.S. Appl. No. 15/204,349, Response filed Feb. 27, 2019 to Non Final Office Action Mailed Nov. 27, 2018, 10 pgs.

U.S. Appl. No. 15/204,349, Final Office Action mailed Apr. 22, 2019, 16 pgs.

U.S. Appl. No. 15/204,349, Response filed Jun. 24, 2019 to Final Office Action mailed Apr. 22, 2019, 12 pgs.

U.S. Appl. No. 15/204,349, Advisory Action mailed Jul. 9, 2019, 5 pgs.

U.S. Appl. No. 15/299,694, Restriction Requirement mailed Aug. 6, 2018, 6 pgs.

U.S. Appl. No. 15/299,694, Response filed Oct. 8, 2018 to Restriction Requirement mailed Aug. 6, 2018, 7 pgs.

U.S. Appl. No. 15/299,694, Non Final Office Action mailed Nov. 27, 2018, 15 pgs.

U.S. Appl. No. 15/299,694, Response filed Feb. 27, 2019 to Non-Final Office Action mailed Nov. 27, 2018, 10 pgs.

U.S. Appl. No. 15/299,694, Final Office Action mailed Apr. 22, 2019, 16 pgs.

U.S. Appl. No. 15/299,694, Response filed Jun. 24, 2019 to Final Office Action mailed Apr. 22, 2019, 11 pgs.

U.S. Appl. No. 15/299,694, Advisory Action mailed Jul. 9, 2019, 5 pgs.

U.S. Appl. No. 15/943,354, Preliminary Amendment filed Apr. 3, 2018, 9 pgs.

U.S. Appl. No. 15/943,354, Restriction Requirement mailed Nov. 20, 2019, 8 pages.

U.S. Appl. No. 15/943,354, Response filed Dec. 19, 2019 to Restriction Requirement mailed Nov. 20, 2019, 8 pages.

U.S. Appl. No. 15/943,354, Non Final Office Action mailed Jan. 13, 2020, 6 pages.

U.S. Appl. No. 15/943,354, Non Final Office Action mailed Apr. 20, 2020, 7 pages.

U.S. Appl. No. 15/996,978, Preliminary Amendment filed Jun. 5, 2018, 11 pgs.

U.S. Appl. No. 15/996,978, Restriction Requirement mailed Feb. 7, 2020, 7 pages.

U.S. Appl. No. 15/996,978, Response filed Apr. 6, 2020 to Restriction Requirement mailed Feb. 7, 2020, 8 pages.

U.S. Appl. No. 15/996,978, Restriction Requirement mailed Apr. 16, 2020, 8 pages.

U.S. Appl. No. 15/996,978, Response filed May 1, 2020 to Restriction Requirement mailed Apr. 16, 2020, 8 pgs.

U.S. Appl. No. 15/996,978, Non Final Office Action mailed Jun. 11, 2020, 8 pages.

U.S. Appl. No. 16/517,180, Preliminary Amendment filed Jul. 19, 2019, 12 pgs.

Final Office Action dated Feb. 19, 2021, U.S. Appl. No. 15/996,978, filed Jun. 4, 2018.

Final Office Action dated Jun. 16, 2021, U.S. Appl. No. 15/996,978, filed Jun. 4, 2018.

Non-final Office Action dated Sep. 2, 2021, U.S. Appl. No. 15/996,978, filed Jun. 4, 2018.

Notice of Allowance dated Oct. 6, 2021, U.S. Appl. No. 15/996,978, filed Jun. 4, 2018.

Response to Office Action dated May 18, 2021, U.S. Appl. No. 15/996,978, filed Jun. 4, 2018.

Response to Office Action dated Jul. 20, 2021, U.S. Appl. No. 15/996,978, filed Jun. 4, 2018.

Response to Office Action dated Sep. 22, 2021, U.S. Appl. No. 15/996,978, filed Jun. 4, 2018.

Borchert, Bianca et al., "Lethal Atrioesophageal Fistula After Pulmonary Vein Isolation using High-Intensity Focused Ultrasound (HIFU)" J. Hrthm vol. 5, Issue 1, p. 145-148, Jan. 2008.

(56) References Cited

OTHER PUBLICATIONS

Calkins, Hugh et al., "Temperature Monitoring During Radiofrequency Catheter Ablation Procedures Using Closed Loop Control," Circulation vol. 90, No. 3, p. 1279-1286, Sep. 1994.
Deardorff, Dana L. et al., "Control of interstitial thermal coagulation: Comparative evaluation of microwave and ultrasound applicators," Medical Physics vol. 28, No. 1, p. 104-117, Jan. 2001.
Dinerman, Jay L. et al., "Temperature Monitoring During Radiofrequency Ablation," Journal of Cardiovascular Electrophysiology, vol. 7 No. 2, p. 163-173, Feb. 1996.
Esler, Murray et al., "The future of renal denervation," Autonomic Neuroscience: Basic and Clinical, vol. 204, p. 131-138, May 2017.
Filonenko, E.A. et al., "Heating of Biological Tissues by Two-Dimensional Phased Arrays with Random and Regular Element Distributions," Acoustical Physics, vol. 50 No. 2, p. 222-231, 2004.
Fry, William J., "Action of Ultrasound on Nerve Tissue—A review," The Journal of the Acoustical Society of America, vol. 25 No. 1, p. 1-5, Jan. 1953.
Fry, Frank J., "Precision High Intensity Focusing Ultrasonic Machines for Surgery," High Intensity Focused U.S., 152-156, Sep. 6-7, 1957.
Haines, David, "Biophysics of Ablation: Application to Technology," Journal of Cardiovascular Electrophysiology, vol. 15, No. 10, p. S2-S11, Oct. 2004.
Hynynen, K. et al., "Design of Ultrasonic Transducers for Local Hyperthermia," Ultrasound in Med. & Biol., vol. 7, No. 4, p. 397-402, Feb. 1981.
Hynynen, K. et al., "Temperature measurements during ultrasound hyperthermia," Medical Physics vol. 16, No. 4, p. 618-626, Jul./Aug. 1989.
Jolesz, Ferenc A. et al., "MR Imaging—Controlled Focused Ultrasound Ablation: A Noninvasive Image-Guided Surgery," Magnetic Resonance Imaging Clinics of North America, vol. 13, Issue 3, p. 545-560, 2005.
Kandzari, David A., et al., "Reply to letter to the editor by Kintur Sanghvi, MD; Allen McGrew, DO; and Kiran Hegde, BE, MBA," American Heart Journal, vol. 180, p. e3-e4, Oct. 2016.
Lafon, C. et al., "Design and Preliminary Results of an Ultrasound Applicator for Interstitial Thermal Coagulation," Ultrasound in Medicine & Biology, vol. 24, No. 1, p. 113-122, 1998.
Lewis, Matthew A. et al., "Thermometry and Ablation Monitoring with Ultrasound," Int. J. Hyperthermia vol. 31, Issue 2, p. 163-181, Mar. 2015.
Liu, Xinmeng et al., "Visualization and mapping of the right phrenic nerve by intracardiac echocardiography during atrial fibrillation ablation," Europace vol. 25, p. 1352-1360, 2023.
Mendelsohn, Farrell O., "Microanatomy of the Renal Sympathetic Nervous System," Endovascular Today, p. 59-62, Oct. 2013.

Okamura, Keisuke et al., "Intravascular Ultrasound Can Be Used to Locate Nerves, but not Confirm Ablation, During Renal Sympathetic Denervation," J. Clin. Med. Res., vol. 13, No. 12, p. 556-562, 2021.
Quadri, Syed A. et al., "High-intensity focused ultrasound: past, present, and future in neurosurgery," Neurosurgical Focus, vol. 44, No. 2, p. 1-9, Feb. 2018.
Ross, Anthony B. et al., "Highly directional transurethral ultrasound applicators with rotational control for MRI-guided prostatic thermal therapy," Physics in Medicine & Biology, vol. 49, p. 189-204, Jan. 2004.
Sakaoka, Atsushi, et al., "Accurate Depth of Radiofrequency-Induced Lesions in Renal Sympathetic Denervation Based on a Fine Histological Sectioning Approach in a Porcine Model," Cir. Cardiovasc. Interv., vol. 11, p. 1-8, 2018.
Sanghvi, Kintur et al., "Rationale and design for studies of renal denervation in the absence (SPYRAL HTN OFF-MED) and presence (SPYRAL HTN ON-MED) of antihypertensive medications," American Heart Journal, vol. 180, p. e1-e2. Oct. 2016.
Satou, Shunsuke et al., "Observation of renal sympathetic nerves by intravascular ultrasound," Hypertension Research vol. 42, p. 1092-1094, 2019.
Schmidt, Boris et al., "Balloon Catheters for Pulmonary Vein Isolation," Herz vol. 33, p. 580-584, 2008.
Smith, Nadine Barrie et al., "Transrectal Ultrasound Applicator for Prostate Heating Monitored Using MRI Thermometry," Int. J. Radiation Oncology Biol. Phys. vol. 43, No. 1, p. 217-225, 1998.
Stauffer, P.R. et al., "13 Interstitial Heating Technologies," Thermoradiotherapy and Thermochemotherapy, p. 279-320, 1995.
Swanson, David K. et al., "Tissue temperature Feedback Control of Power, The Key to Successful Ablation," Innovations, vol. 6 No. 4, p. 276-282, Jul./Aug. 2011.
Tabei, Makoto et al., "A k-space method for coupled first-order acoustic propagation equations," J. Acoust. Soc. Am., vol. 111, No. 1, pt. 1, p. 53-63, Jan. 2002.
Tzafriri, Abraham R. et al., "Innervation Patterns May Limit Response to Endovascular Renal Denervation," Journal of the American College of Cardiology, vol. 64, No. 11, p. 1079-1087, Sep. 2014.
Umemura, Shin-ichiro, "Focused ultrasound transducer for thermal treatment," International Journal of Hyperthermia, vol. 31, No. 2, p. 216-221, 2015.
Wan, Hong et al., "Thermal Dose Optimization for Ultrasound Tissue Ablation," IEE Transactions on Ultrasonics, Ferroelectrics, and Frequency Control, vol. 46, No. 4, p. 913-928, Jul. 1999.
Zivin, Adam, et al., "Temperature Monitoring versus Impedance Monitoring during RF Catheter Ablation," Radiofrequency Catheter Ablation of Cardiac Arrhythmias, Basic Concepts and Clinical Applications, Second Edition, Edited by Shoei K. Stephen Huang, MD & David J. Wilber, MD, p. 103-112, 2000.

\* cited by examiner

METHOD AND APPARATUS FOR TREATMENT OF HYPERTENSION THROUGH PERCUTANEOUS ULTRASOUND RENAL DENERVATION

CROSS-REFERENCE TO RELATED APPLICATIONS

This application is a continuation of U.S. patent application Ser. No. 16/055,014, filed Aug. 3, 2018, pending, which is a continuation of U.S. patent application Ser. No. 13/826,645, filed Mar. 14, 2013, now U.S. Pat. No. 10,039,901, which is a continuation of U.S. patent application Ser. No. 13/503,109, filed May 30, 2012, now U.S. Pat. No. 9,981,108, which is a national phase of International PCT Patent Application Serial No. PCT/US10/54637, filed Oct. 29, 2010, which claims the benefit of U.S. Provisional Patent Application Nos. 61/256,429, filed Oct. 30, 2009 and 61/292,618, filed Jan. 6, 2010, the entire contents of each of which are incorporated by referenced herein. The present application is also related to U.S. patent application Ser. No. 14/731,347, filed Jun. 4, 2015, now U.S. Pat. No. 9,943,666.

BACKGROUND OF THE INVENTION

Successful treatment of hypertension is important for many reasons. For example, successful treatment of hypertension has significant clinical benefits in preventing or limiting conditions caused by or exacerbated by hypertension, such as renal disease, arrhythmias, and congestive heart failure, to name a few. While drug therapy can be used to treat hypertension, it is not always successful. Some people are resistant to drug therapy treatment or experience significant side effects from drug therapy treatment.

Hypertension can be treated by inactivating conduction of the renal nerves surrounding the renal artery. Sympathetic renal nerve activity plays a significant role in the initiation and maintenance of hypertension. When the brain perceives increased renal nerve activity, signaling low blood volume or a drop in blood pressure, it compensates by increasing sympathetic nerve activity to the heart, the liver, and the kidneys, which results in increased cardiac output; insulin resistance; and most importantly, increased renin production by the kidneys. Renin stimulates the production of angiotension, which causes blood vessels to constrict, resulting in increased blood pressure and stimulates the secretion of aldosterone. Aldosterone causes the kidneys to increase the reabsorption of sodium and water into the blood, increasing blood volume thereby further increasing blood pressure.

It has been established for years that surgically cutting renal nerves results in a decrease in blood pressure and water retention to normal levels; thereby allowing the patients' heart, liver, and kidneys to also return to healthier functioning. It has also been shown a disruption of the renal nerves has no serious ill effects. However, surgically cutting the renal nerves requires a major surgical procedure with risks of undesirable side effects. It would be desirable to produce the same result without major surgery.

In order to explain the difficulties associated with accomplishing this task without causing other damage, the anatomy of the renal arteries and nerves will be described now. Shown in FIG. 1 is an illustration of the renal nerves 8 that surround the renal artery 10, which is connected to the kidney 6. The sympathetic renal nerves 8 include both the afferent sensory renal nerves from the kidney 6 to the brain and the efferent sympathetic renal nerves from the brain to the kidney 6. In addition, FIG. 2 shows a cross-section of a renal artery 10. The renal artery wall includes layers: the intima 3, which includes an inner single layer of endothelial cells; the media 5, which is in the center of the artery wall; and the adventitia 4, which is the outside layer. Also shown are the renal nerves 8 that lie within the adventitia 4, on the surface of the renal artery 10, and adjacent to the renal artery 10. As can be seen from these two figures, the renal nerves 8 surround the renal artery 10. Different individuals have the renal nerves 8 in different locations around the renal artery. Thus, the renal nerves may be at different radial distances R from the central axis A of the renal artery, and also may be at different locations around the circumference C of the renal artery. It is not practical to locate the renal nerves by referring to anatomical landmarks.

Moreover, it is difficult or impossible to locate individual renal nerves using common in vivo imaging technology.

The inability to locate and target the renal nerves 8 makes it difficult to disconnect the sympathetic renal activity using non-surgical techniques without, causing damage to the renal artery 10 or causing other side effects. For example, attempts to apply energy to the renal nerves can cause effects such as stenosis, intimal hyperplasia, and necrosis. Other side effects can include thrombosis, platelet aggregation, fibrin clots and vasoconstriction. In addition, the inability to target and locate the renal nerves 8 makes it difficult to ensure that sympathetic renal nerve activity has been discontinued enough to achieve an acceptable therapeutic treatment.

U.S. Pat. No. 7,617,005 suggests the use of a radio frequency ("RF") emitter connected to a catheter, which is inserted in the renal artery. The RP emitter is placed against the intima and the RF energy is emitted to heat the renal nerves to a temperature that reduces the activity of renal nerves which happen to lie in the immediate vicinity of the emitter. In order to treat all the renal nerves surrounding the renal arteries, the AF emitter source must be repositioned around the inside of each renal artery multiple times. The emitter may miss some of the renal nerves, leading to an incomplete treatment. Moreover, the RF energy source must contact the intima to be able to heat the renal nerves, which may cause damage or necrosis to the single layer endothelium and the intima, potentially causing intimal hyperplasia, renal artery stenosis, and renal artery dissection.

The '005 patent also suggests the use of high-intensity focused ultrasound to deactivate the renal nerves. The described high-intensity focused ultrasound energy source assertedly emits ultrasound energy in a 360° pattern around the axis of the renal artery, and does not need to contact the intima 3. However, the high-intensity focused ultrasound source applies concentrated energy in a thin focal ring surrounding the artery. It is difficult or impossible to align this thin ring with the renal nerves because it is difficult or impossible to visualize and target the renal nerves with current technology, and because the renal nerves may lie at different radial distances from the central axis of the renal artery. The latter problem is aggravated in patients who have renal arteries with large variations in shape or thickness. Moreover, the thin focal ring can encompass only a sail segment of each renal nerve along the lengthwise direction of the nerves and artery. Since nerves tend to re-grow, a small treatment zone allows the nerves to reconnect in a shorter period of time.

For many years ultrasound has been used to enhance cell repair, stimulate the growth of bone cells, enhance delivery of drugs to specific tissues, and to image tissue within the body. In addition, high-intensity focused ultrasound has been used to heat and ablate tumors and tissue within the body. Ablation of tissue has been performed nearly exclusively by high-intensity focused ultrasound because the emitted ultrasound energy is focused on a specific location to allow precise in-depth tissue necrosis without affecting surrounding tissue and intervening structures that the ultrasound energy must pass through.

U.S. Pat. No. 6,117,101, to Diederich, discusses use of highly collimated ultrasound energy rather than high intensity focused ultrasound for ablating tissue to create a scar ring within the pulmonary vein for blocking the conduction of electrical signals to the heart.

US Patent Publication No. 20100179424 (application Ser. No. 12/684,067), the disclosure of which is incorporated by reference herein, uses unfocused ultrasound for the treatment of mitral valve regurgitation. In the '474 Publication, unfocused ultrasound energy is used to heat and shrink the collagen associated with the mitral annulus. This apparatus uses an inflatable balloon in order to place the ultrasound transducer into the correct location, thereby targeting the mitral annulus. In this apparatus, a part of the balloon contacts the tissue to be heated.

BRIEF SUMMARY OF THE INVENTION

One aspect of the invention provides apparatus for inactivating renal nerve conduction in a human or non-human mammalian subject. The apparatus according to this aspect of the invention preferably includes an ultrasound transducer adapted for insertion into a renal artery of the mammalian subject. The ultrasound transducer desirably is arranged to transmit unfocused ultrasound energy. The apparatus according to this aspect of the invention desirably also includes an actuator electrically connected to the transducer. The actuator most preferably is adapted to control the ultrasound transducer to transmit unfocused ultrasound energy into an impact volume of at least approximately 0.5 $cm^3$, encompassing the renal artery so that the unfocused ultrasound energy is applied at a therapeutic level sufficient to inactivate conduction of renal nerves throughout the impact volume. As discussed further below, such therapeutic level is below the level required for tissue ablation.

The apparatus may further include a catheter with a distal end and a proximal end, the transducer being mounted to the catheter adjacent the distal end, the catheter and transducer being constructed and arranged to allow a substantial flow of blood through the renal artery while the ultrasound transducer is positioned within the renal artery. The catheter may be constructed and arranged to hold the transducer out of contact with the wall of the renal artery. The catheter may have an expansible element such as a balloon, wire basket or the like mounted adjacent the distal end. For example, the transducer may be adapted to transmit the ultrasound energy in a 360° cylindrical pattern surrounding a transducer axis, and the catheter may be constructed and arranged to hold the axis of the transducer generally parallel to the axis of the renal artery.

A further aspect of the invention provides methods for inactivating renal nerve conduction in a mammalian subject. A method according to this aspect of the invention desirably includes the steps of inserting an ultrasound transducer into a renal artery of the subject and actuating the transducer to transmit therapeutically effective unfocused ultrasound energy into an impact volume of at least approximately 0.5 $cm^3$ encompassing the renal artery. The ultrasound energy desirably is applied so that the therapeutically effective unfocused ultrasound energy inactivates conduction of all the renal nerves in the impact volume. For example, the step of actuating the transducer may be so as to maintain the temperature of the renal artery well below 65° C. while heating the solid tissues within the impact volume, including the renal nerves in the impact volume, to above 42° C.

Because the impact volume is relatively large, and because the tissues throughout the impact volume preferably reach temperatures sufficient to inactivate nerve conduction, the preferred methods according to this aspect of the invention can be performed successfully without determining the actual locations of the renal nerves, and without targeting or focusing on the renal nerves. The treatment can be performed without measuring the temperature of tissues. Moreover, the treatment preferably is performed without causing stenosis of the renal artery, intimal hyperplasia, or other injuries that would require intervention. The preferred methods and apparatus can inactive relatively long segments of the renal nerves, so as to reduce the possibility of nerve recovery which would re-establish conduction along the inactivated segments.

Further aspects of the invention provide probes which can be used in the method and apparatus discussed above, and apparatus incorporating means for performing the steps of the methods discussed above.

DETAILED DESCRIPTION

Figure 1:
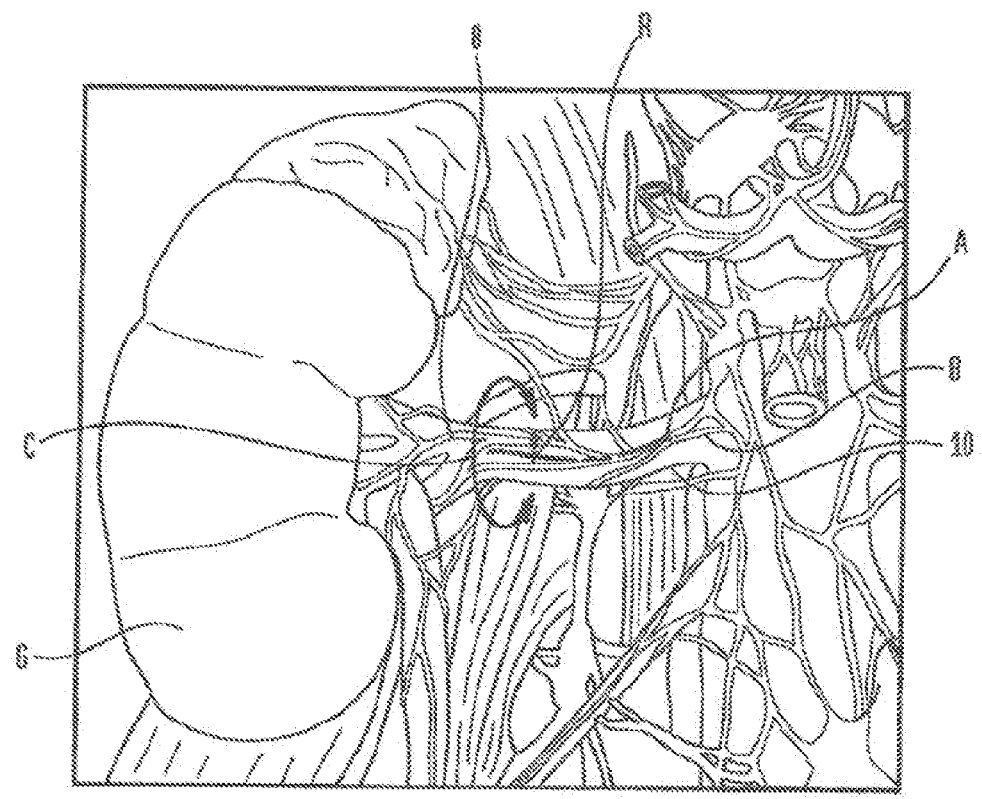
FIG. 1 is an anatomical view of a typical renal artery and associated structure.

Apparatus according to one embodiment of the invention (FIG. 3) includes a sheath 12. The sheath 12 generally may be in the form of an elongated tube having a proximal end 14, a distal end 16 and a proximal-to-distal axis 15. As used in this disclosure with reference to elongated elements for insertion into the body, the term "distal" refers to the end which is inserted into the body first, i.e., the leading end during advancement of the element into the body, whereas the term "proximal" refers to the opposite end. The sheath 12 may be a steerable sheath. Thus, the sheath may include known elements such as one or more pull wires (not shown) extending between the proximal and distal ends of the sheath and connected to a steering control 17 arranged so that actuation of the steering control by the operator flexes the distal end 16 of the sheath in a direction transverse to the axis 15.

Figure 3:
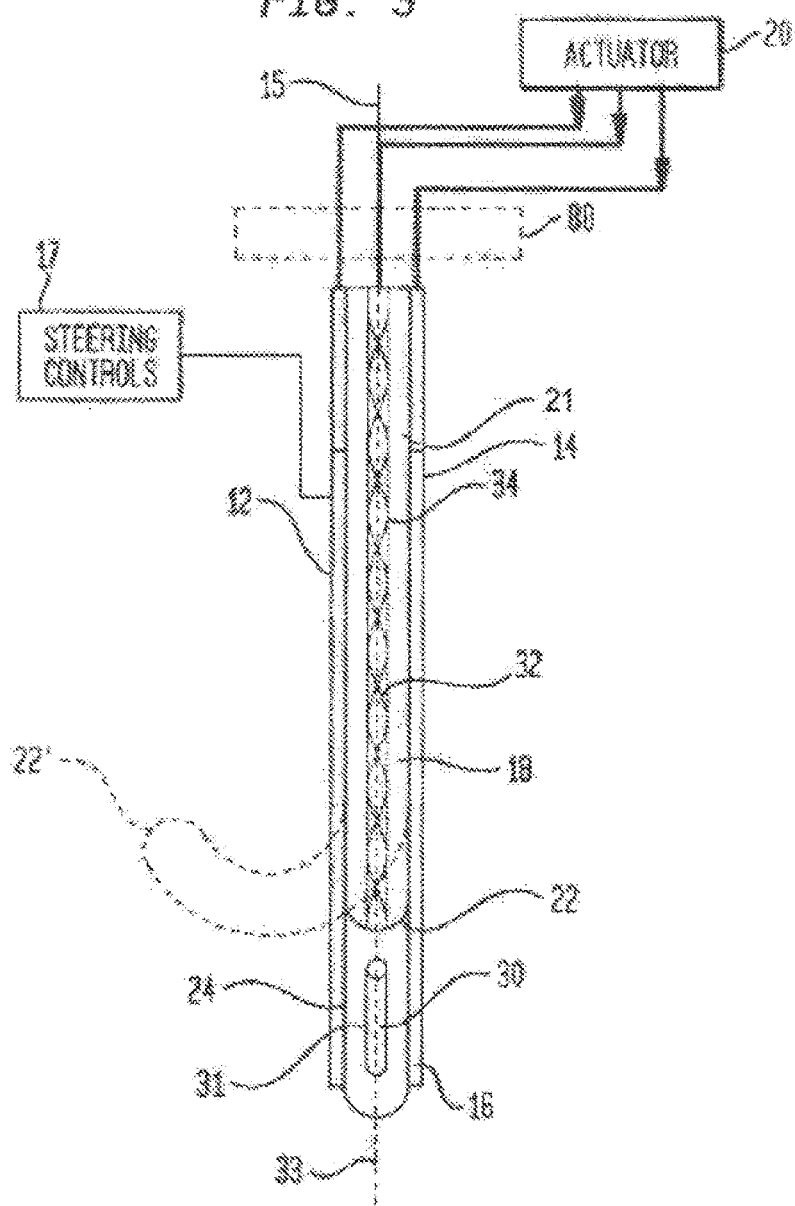
FIG. 3 is a diagrammatic view depicting components of apparatus in accordance with one embodiment of the present invention.

The apparatus also includes a catheter 18 having a proximal end 20, a distal end 22 and a proximal-to-distal axis which, in the condition depicted in FIG. 3 is coincident with the proximal-to-distal axis 15 of the sheath. The proximal end 20 of the catheter desirably is relatively stiff such that it may transmit torque. Thus, by turning the proximal end 20 of the catheter 18, distal end 22 of the catheter 18 can be rotated about the proximal-to-distal axis of the catheter 18.

The distal end 22 of the catheter 18 is preformed so that when the distal end of the catheter is outside of the sheath 12, the distal end tends to assume a hooked configuration as indicated in broken lines at 22' in FIG. 3. In this condition, rotational motion of the distal end 22' will swing the curved section around the proximal-to-distal axis. Thus, by rotating the proximal end of the catheter 18, the distal end 22' of the catheter 18 can be positioned in any radial direction.

Catheter 18 has a balloon 24 mounted at the distal end 22. In its inflated condition (FIG. 4), balloon 24 has a partially non-circular profile in which one part 82 of the balloon is smaller in diameter than the renal artery, whereas another part 80 of the balloon 24 is noncircular in shape. The noncircular part has a major diameter $D_{MAX}$ equal to or just slightly lose than the internal diameter of the renal artery, and has a minor diameter $D_{MIN}$ smaller than the major diameter.

An ultrasound transducer 30 (FIGS. 3 and 5) is mounted adjacent the distal end 22 of catheter 18 within balloon 24. Transducer 30, which is desirably formed from a ceramic piezoelectric material, is of a tubular shape and has an exterior emitting surface 31 in the form of a cylindrical surface of revolution about the proximal-to-distal axis 33 of the transducer 30. The transducer 30 typically has an axial length along axis 31 of approximately 2-10 mm, and preferably 6 mm. The outer diameter of the transducer 30 is approximately 1.5-3 ma in diameter, and preferably 2 mm. The physical structure of the transducer and its mounting to the catheter may be, for example, as described in U.S. Pat. Nos. 7,540,846 and 6,763,722, the disclosures of which are incorporated by reference herein. The transducer 30 also has conductive coatings (not shown) on its interior and exterior surfaces. Thus, the transducer may be physically mounted on a metallic support tube 84 (FIG. 5), which in turn is mounted to the catheter. The coatings are electrically connected to ground and signal wires 32. Wires 32 extend from the transducer 30 through a lumen 34. The lumen 34 extends between the proximal end and the distal end of a catheter 18, while the wires 32 extend from the transducer 30, through the lumen 34, to the proximal end of the 14 catheter 18.

Transducer 30 is arranged so that ultrasonic energy generated in the transducer is emitted principally from the exterior emitting surface. Thus, the transducer may include features arranged to reflect ultrasonic energy directed toward the interior of the transducer so that the reflected energy reinforces the ultrasonic vibrations at the exterior surface. For example, support tube 84 and transducer 30 may be configured so that the interior surface of the transducer 30 is spaced apart from the exterior surface of the support tube, which is formed from metal, by a gap (not shown). The distance across the gap, between the interior surface of the transducer and the exterior surface of the support tube may be one half the wavelength of the ultrasound energy emitted by the transducer, to promote efficient operation, of the transducer 30. In this embodiment, the ultrasound energy generated by the transducer 30 is reflected at the water gap to reinforce ultrasound energy propagating from the transducer 30, thereby ensuring the ultrasound energy is directed outwardly from an external surface of the transducer 30.

Transducer 30 is also arranged to convert ultrasonic waves impinging on the exterior surface 31 into electrical signals on wires 32. Stated another way, transducer 30 can act either as an ultrasonic emitter or an ultrasonic receiver.

The transducer 30 is designed to operate, for example, at a frequency of approximately 1 MHz to approximately a few tons of MHz, and typically at approximately 9 MHz. The actual frequency of the transducer 30 typically varies somewhat depending on manufacturing tolerances. The optimal actuation frequency of the transducer may be encoded in a machine-readable or human-readable element (not shown) such as a digital memory, bar code or the like affixed to the catheter. Alternatively, the readable element may encode a serial number or other information identifying the individual catheter, so that the optimum actuation frequency may be retrieved from a central database accessible through a communication link such as the internet.

Figure 6:
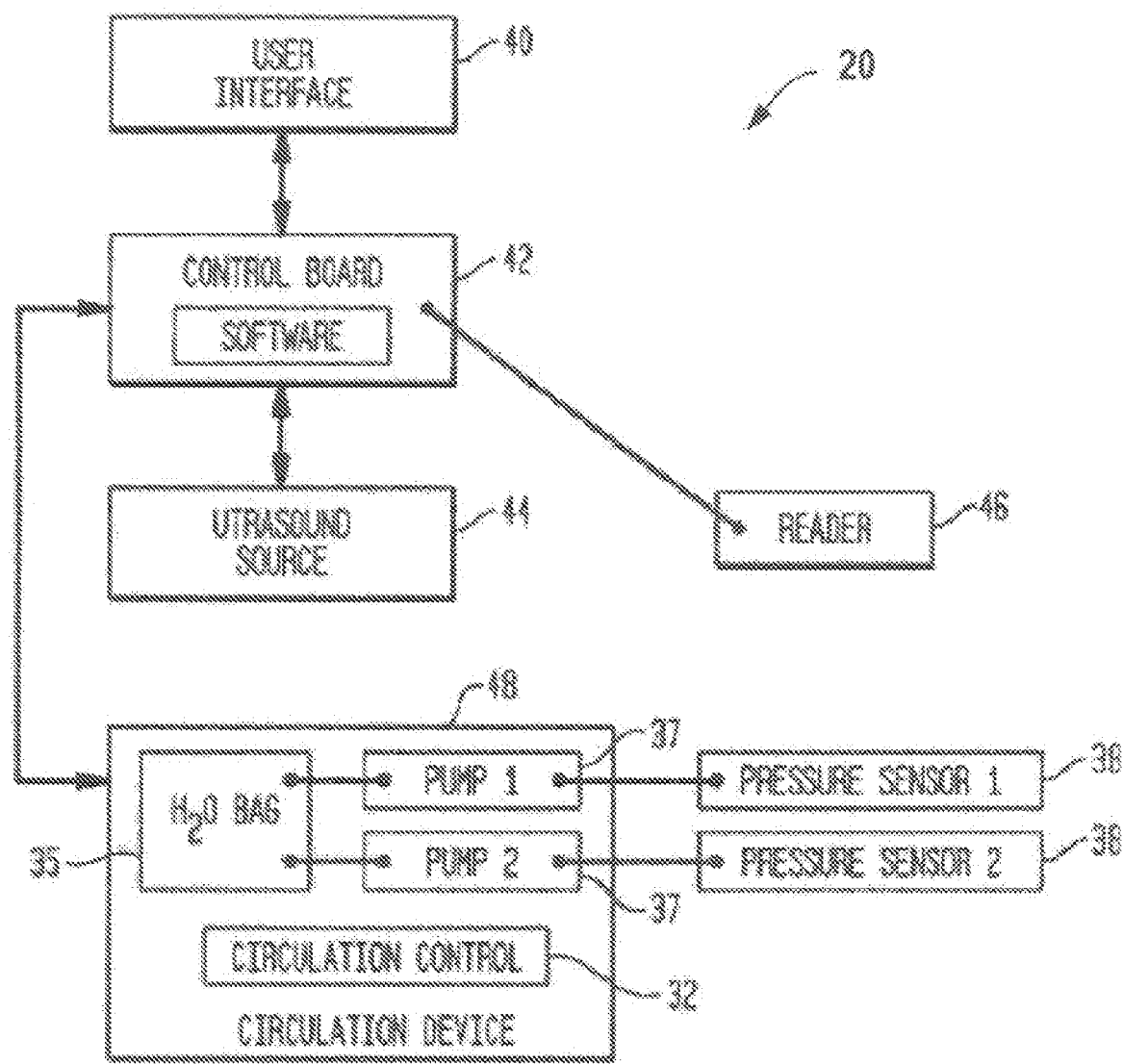
FIG. 6 is a functional, block diagrammatic view depicting portions of a component used in the apparatus of FIGS. 3 and 4.

An ultrasound system 20, also referred to herein as an actuator, is releasably connected to catheter 18 and transducer 30 through a plug connector 88 (FIG. 3). As seen in FIG. 6, ultrasound system 20 may include a user interface 40, a control board 42 incorporating a programmable control device such as a programmable microprocessor (not shown), an ultrasound excitation source 44, and a circulation device 48. The user interface 40 interacts with the control board 42, which interacts with the excitation source 44 to cause transmission of electrical signals at the optimum actuation frequency of the transducer to the transducer 30 via wires 32. The control board 42 and ultrasound source 44 are arranged to control the amplitude and timing of the electrical signals so as to control the power level and duration of the ultrasound signals emitted by transducer 30. Excitation source 44 is also arranged to detect electrical signals generated by transducer 30 and appearing on wires 32 and communicate such signals to control board 42.

The circulation device 48 is connected to lumens (not shown) within catheter 18 which in turn are connected to balloon 24. The circulation device is arranged to circulate a liquid, preferably an aqueous liquid, through the catheter 18 to the transducer 30 in the balloon 24. The circulation device 48 may include elements such as a tank for holding the circulating coolant 35, pumps 37, a refrigerating coil (not shown), or the like for providing a supply of liquid to the interior space of the balloon 24 at a controlled temperature, desirably at or below body temperature. The control board 42 interfaces with the circulation device 48 to control the flow of fluid into and out of the balloon 24. For example, the control board 42 may include motor control devices linked to drive motors associated with pumps for controlling the speed of operation of the pumps 37. Such motor control devices can be used, for example, where the pumps 37 are positive displacement pumps, such as peristaltic pumps. Alternatively or additionally, the control circuit may include structures such as controllable valves connected in the fluid circuit for varying resistance of the circuit to fluid flow (not shown). The ultrasound system 20 may further include two pressure sensors 38, to monitor the liquid flow through the catheter 18. One pressure sensor monitors the flow of the liquid to the distal catheter 18 to determine if there is a blockage while the other monitors leaks in the catheter 10. While the balloon is in an inflated state, the pressure sensors 38 maintain a desired pressure in the balloon preferably at approximately 3 pounds per square inch (20 KPa).

The ultrasound system 20 incorporates a reader 46 for reading a machine-readable element on catheter 18 and conveying the information from such element to control board 46. As discussed above, the machine-readable element on the catheter may include information such as the operating frequency of the transducer 30 in a particular catheter 10, and the control board 42 may use this information to set the appropriate frequency for exciting the transducer. Alternatively, the control board may be arranged to actuate excitation source 44 to measure the transducer operating frequency by energizing the transducer at a low power level while scanning the excitation frequency over a pre-determined range of frequencies for example 8.5 Mhz-9.5 Mhz, and monitoring the response of the transducer to such excitation.

The ultrasonic system 20 may be similar to that disclosed in U.S. Provisional Patent Application No. 61/256,002, filed Oct. 29, 2009, entitled "METHOD AND APPARATUS FOR PERCUTANEOUS TREATMENT OF MITRAL VALVE REGURGITATION (PMVR)" the disclosure of which is incorporated by reference herein.

Figure 7:
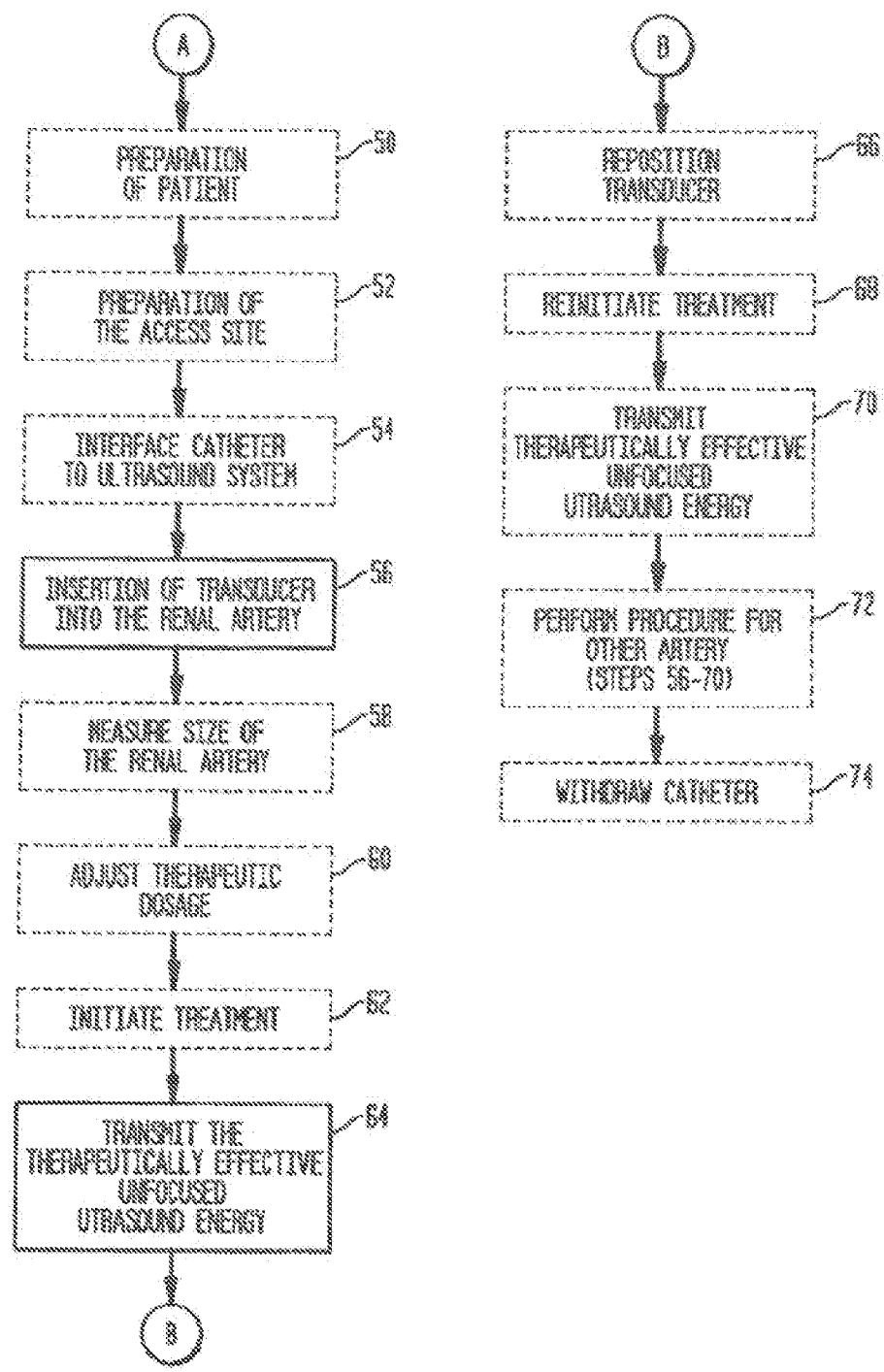
FIG. 7 is a flow chart depicting the steps used in a method according to one embodiment of the present invention.
Figure 8:
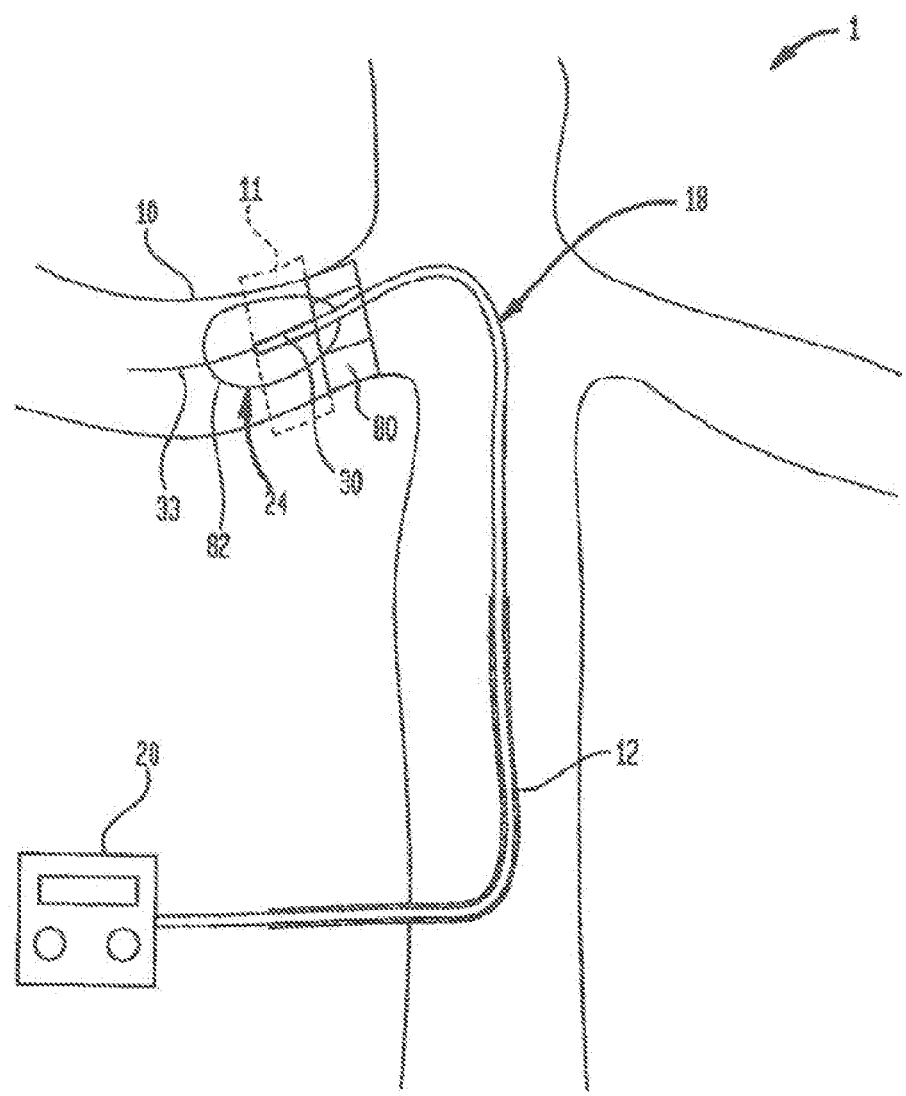
FIG. 8 is a diagrammatic view depicting portions of the apparatus of FIGS. 3 and 4 during operation in accordance with the method of FIG. 7.

A method according to an embodiment of the present invention is depicted in flowchart form in FIG. 7. After preparing a human or non-human mammalian subject such as a patient (step 50), preparation of an arterial access site such as a location on the femoral artery (step 52), and connecting the catheter 18 to the ultrasound system 20 (step 54), the ultrasound transducer 30 in inserted into the renal artery (step 56) by inserting the distal end of the sheath 12 through the access site into the aorta. While the distal end of the sheath is positioned within the aorta, the catheter 18 is advanced within the sheath until the distal end of the catheter projects from the sheath as schematically depicted in FIG. 8. Because the distal end 22 of the catheter 18 is pre-formed like a hook, the distal end 22 of the catheter 18 may slide into the renal artery 10 then the tip is rotated inside the aorta towards the renal artery 10 branches and than slightly pushed forward and pulled backwards. This action is facilitated by the typical angle of the renal artery/aorta bifurcation. Based on the hooked shape of the distal end 22, the distal end 22 of the catheter 18 may tend to catch in the renal artery 10 side branch when pulled back inside the aorta. The balloon 24 on the catheter desirably is maintained in a deflated condition until the distal end of the catheter is disposed at a desired location within the renal artery. During insertion of the catheter 18 and the transducer 30 (step 56), the physician may verify the placement of the transducer 30 to be within the renal artery 10, although before the kidney 6 or any branches of the renal artery 10 that may exist. Such verification can be obtained using x-ray techniques such as fluoroscopy.

Figure 4:
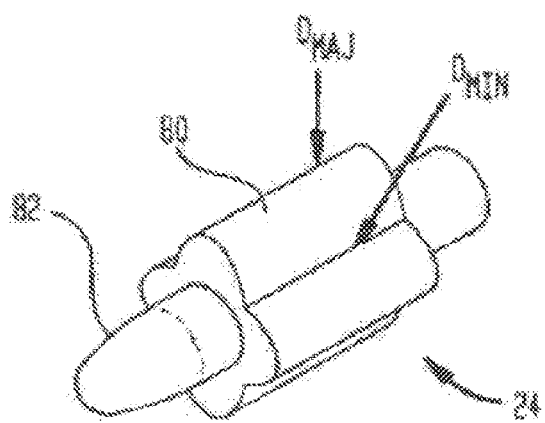
FIG. 4 is a fragmentary diagrammatic perspective view depicting a portion of the apparatus shown in FIG. 3.
Figure 5:
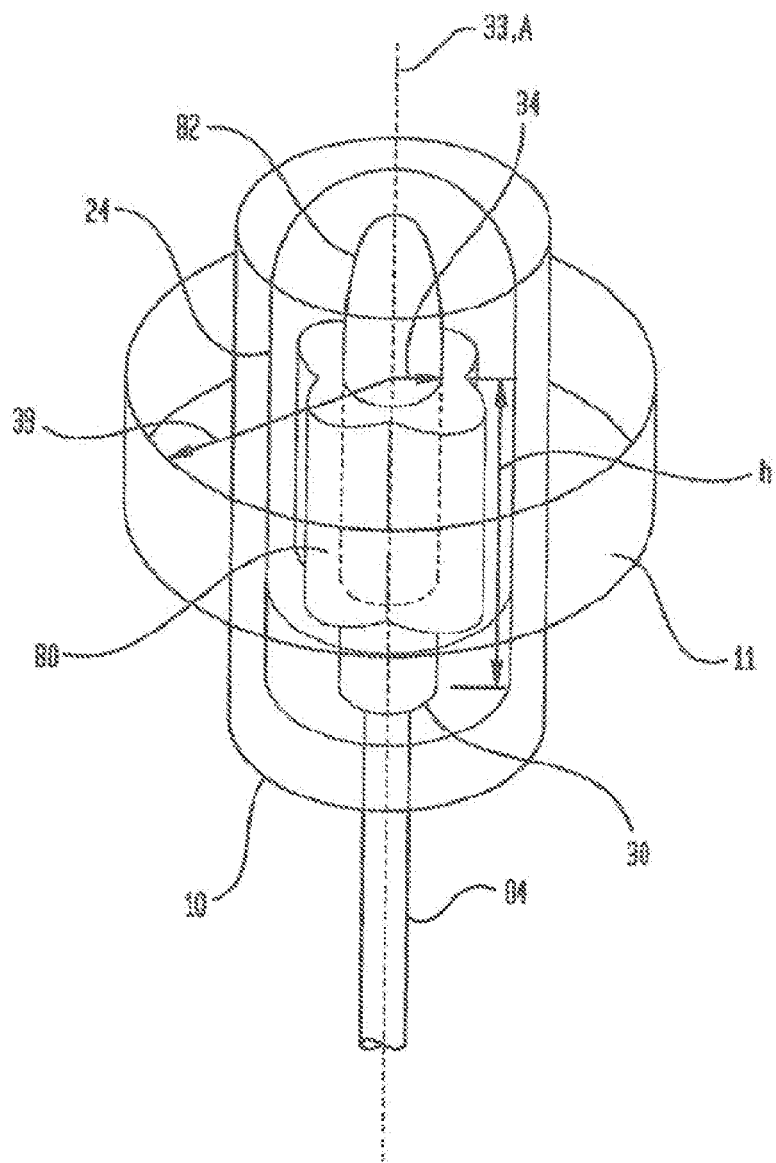
FIG. 5 is a diagrammatic view depicting a portion of the apparatus of FIGS. 3 and 4 in conjunction with a renal artery.

Once the distal end of the catheter is in position within a renal artery, pumps 31 bring balloon 24 to an inflated condition as depicted in FIGS. 4 and 5. In this condition, the non-circular portion 60 of the balloon engages the artery wall, and thus centers transducer 30 within the renal artery, with the axis 33 of the transducer (FIG. 5) approximately coaxial with the axis A of the renal artery. However, the balloon does not block blood flow through the renal artery. In this condition, the circulation device 48 maintains a flow of cooled aqueous liquid into and out of balloon 24, so as to cool the transducer 30. The cooled balloon also tends to cool the interior surface of the renal artery. Moreover, the continued flow of blood through the renal artery helps to cool the interior surface of the renal artery. The liquid flowing within the balloon may include a radiographic contrast agent to aid in visualization of the balloon and verification of proper placement.

In the next step 58, the ultrasound system 20 uses transducer 30 to measure the size of the renal artery 10. Control board 42 and ultrasound source 44 actuate the transducer 30 to "ping" the renal artery 10 with a low-power ultrasound pulse. The ultrasonic waves in this pulse are reflected by the artery wall onto transducer 30 as echoes. Transducer 30 converts the echoes to echo signals on wires 32. The ultrasound system 20 then determines the size of the artery 10 by analyzing the echo signals. For example, the ultrasound system 20 may determine the time delay between actuation of the transducer to produce the "ping" and the return of echo signals. In step 60, the ultrasound system 20 uses the measured artery size to set the acoustic power to be delivered by transducer 30 during application of therapeutic ultrasonic energy in later steps. For example, control board 42 may use a lookup table correlating a particular echo delay (and thus artery diameter) with a particular power level. Generally, the larger the artery diameter, the more power should be used. Variations in the shape of the renal artery 10, or in the centering of the transducer 30, may cause a range of time delay in the echo signals. The ultrasound system 20 may take an average of the range to determine the average size of the renal artery 10 and make adjustments to the power level based on the average size.

The physician then initiates the treatment (step 60) through the user interface 40. In the treatment (step 64), the ultrasonic system or actuator 20, and particularly the control board 42 and ultrasonic source 44, actuate transducer 30 to deliver therapeutically effective ultrasonic waves to an impact volume 11 (FIG. 5). The ultrasound energy transmitted by the transducer 30 propagates generally radially outwardly and away from the transducer 30 encompassing a full circle, or 360° of arc about the proximal-to-distal axis 33 of the transducer 30 and the axis A of the renal artery.

The selected operating frequency, unfocused characteristic, placement, size, and the shape of the ultrasound transducer 30 allows the entire renal artery 10 and renal nerves to lie within the "near field" region of the transducer 30. Within this region, an outwardly spreading, unfocused omni-directional (3600) cylindrical beam of ultrasound waves generated by the transducer 30 tends to remain collimated and has an axial length approximately equal to the axial length of the transducer 30. For a cylindrical transducer, the radial extent of the near field region is defined by the expression $L^2/\lambda$, where L is the axial length of the transducer 30 and $\lambda$ is the wavelength of the ultrasound waves. At distances from the transducer 30 surface greater than $L^2/\lambda$, the beam begins to spread axially to a substantial extent. However, for distances less than $L^2/\lambda$, the beam does not spread axially to any substantial extent. Therefore, within the near field region, at distances less than $L^2/\lambda$, the intensity of the ultrasound energy decreases linearly, in proportion to distance from the transducer 30 surface, as the unfocused beam spreads radially. As used in this disclosure, the term "unfocused" refers to a beam, which does not increase in intensity in the direction of propagation of the beam away from the transducer 30.

The impact volume 11 is generally cylindrical and coaxial with the renal artery. It extends from the transducer surface to an impact radius 39, where the intensity of the ultrasonic energy is too small to heat the tissue to the temperature range that will cause inactivation of the renal nerves 8. The impact radius 39 is determined by the dosage of ultrasound energy transmitted from the transducer 30. The volume V of impact volume 11 is determined by the following equation:

$$V = \pi r_2^2 h - \pi r_1^2 h$$

where
   $r_1$ = the radius of the transducer 30
   $r_2$ = the radius of the impact zone 11
   h = length of the transducer 30

As discussed above, the length of the transducer 30 may vary between 2 mm and 10 mm, but is preferably 6 mm to provide a wide inactivation zone of the renal nerves. The diameter of the transducer 30 may vary between 1.5 mm to 3.0 mm, and is preferably 2.0 mm. The dosage is selected not only for its therapeutic effect, but also to allow the radius 39 of the impact volume 11 to be between preferably 5 mm to 7 mm in order to encompass the renal artery 10, and adjacent renal nerves, all of which lie within an average radius of 3-4 mm, without transmitting damaging ultrasound energy to structures beyond the renal artery 10. This will result in an impact volume 11 of at least 0.5 cm$^3$, with the length of renal nerve inactivation closely corresponding to the length of the transducer 32.

The power level desirably is selected so that throughout the impact volume, solid tissues are heated to about 42° C. or more for at several seconds or more, but desirably all of the solid tissues, including the intima of the renal artery remain well below 65° C. Thus, throughout the impact region, the solid tissues (including all of the renal nerves) are brought to a temperature sufficient to inactivate nerve conduction but below that which causes rapid necrosis of the tissues.

Figure 2:
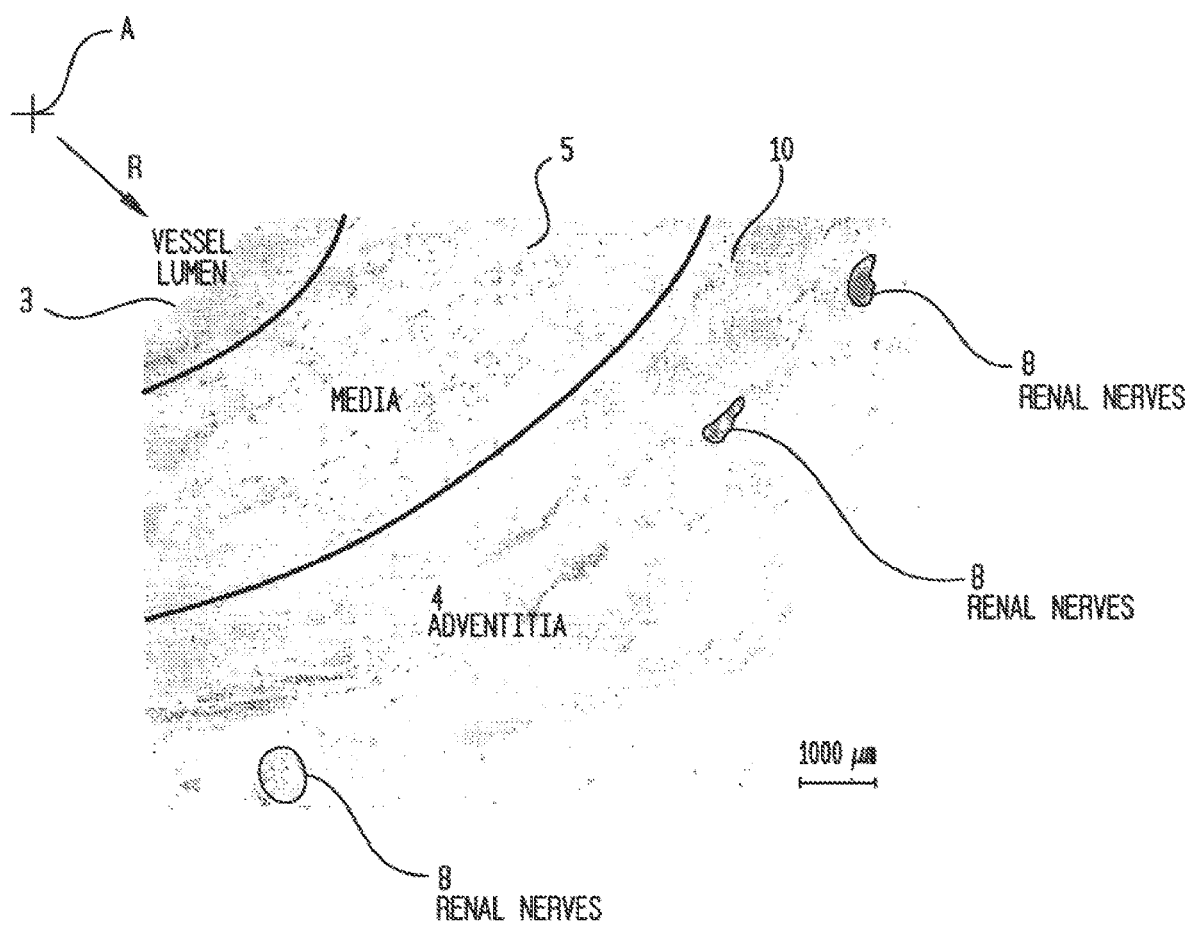
FIG. 2 is a diagrammatic sectional view depicting a portion of a renal artery and nerves.

Research shows that nerve damage occurs at much lower temperatures and much faster than tissue necrosis. See Bunch, Jared. T. et al. "Mechanisms of Phrenic Nerve Injury During Radiofrequency Ablation at the Pulmonary Vein Orifice, *Journal of Cardiovascular Electrophysiology*, Volume 16, Issue 12, pg. 1318-1325 (Dec. 8, 2005), incorporated by reference herein. Since, necrosis of tissue typically occurs at temperatures of 65° C. or higher for approximately 10 sec or longer while inactivation of the renal nerves 8 typically occurs when the renal nerves 8 are at temperatures of 42° C. or higher for several seconds or longer, the dosage of the ultrasound energy is chosen to keep the temperature in the impact volume 11 between those temperatures for several seconds or longer. The dosage of ultrasonic energy desirably is also less than that required to cause substantial shrinkage of collagen in the impact volume. Operation of the transducer thus provides a therapeutic dosage, which inactivates the renal nerves 8 without causing damage to the renal artery 10, such as, stenosis, intimal hyperplasia, intimal necrosis, or other injuries that would require intervention. The continued flow of blood across the inside wall of the renal artery 10 ensures the intimal layer 3 (FIG. 2) of the renal artery is cooled. This allows the ultrasound energy transmitted at the therapeutic dosage to be dissipated and converted to heat principally at the outer layers of the renal artery 10 and not at the intimal layer 3. In addition, the circulation of cooled liquid through the balloon 24 containing the transducer 30 may also help reduce the heat being transferred from the transducer 30 to the intimal layer 3 and to the blood flowing past the transducer. Hence, the transmitted therapeutic unfocused ultrasound energy does not damage the intima and does not provoke thrombus formation, providing a safer treatment.

In order to generate the therapeutic dosage of ultrasound energy, the acoustic power output of the transducer typically 1.9 approximately 10 watts to approximately 100 watts, more typically approximately 20 to approximately 30 watts. The duration of power application typically is approximately 2 seconds to approximately a minute or more, wore typically approximately 10 seconds to approximately 20 seconds. The optimum dosage used with a particular system to achieve the desired temperature levels may be determined by mathematical modeling or animal testing.

The impact volume 11 of the unfocused ultrasound energy encompasses the entire renal artery 10, including the adventitia and closely surrounding tissues, and hence encompasses all of the renal nerves surrounding the renal artery. Therefore, the placement in the renal artery 10 of the transducer 30 may be indiscriminate in order to inactivate conduction of all the renal nerves 8 surrounding the renal arteries 10 in the subject. As used in this disclosure "indiscriminate" and "indiscriminately" mean without targeting, locating, or focusing on any specific renal nerves.

Optionally, the physician may then reposition the catheter 18 and transducer 30 along the renal artery (step 66) and reinitiate the treatment 68 to retransmit therapeutically effective unfocused ultrasound energy (step 70). This inactivates the renal nerves at an additional location along the length of the renal artery, and thus provides a safer and more reliable treatment. The repositioning and retransmission steps optionally can be performed multiple times. Next the physician moves the catheter 18 with the transducer 30 to the other renal artery 10 and performs the entire treatment again for that artery 10, (step 72). After completion of the treatment, the catheter 18 is withdrawn from the subject's body (step 74).

Numerous variations and combinations of the features discussed above can be utilized. For example, the ultrasound system 20 may control the transducer 30 to transmit ultrasound energy in a pulsed function during application of therapeutic ultrasonic energy. The pulsed function causes the ultrasound transducer 30 to emit the ultrasound energy at a duty cycle of, for example, 50%. Pulse modulation of the ultrasound energy is helpful in limiting the tissue temperature while increasing treatment times.

In a further variant, the steps of measuring the renal artery size and adjusting the dose (steps 58 and 72) may be omitted. In this instance, the transducer is simply operated at a preset power level sufficient for the renal arteries of an average subject. In a further variant, the renal artery diameter can be measured by techniques other than actuation of transducer 30 as, for example, by radiographic imaging using a contrast agent introduced into the renal artery or magnetic resonance imaging or use of a separate ultrasonic measuring catheter. In this instance, the data from the separate measurement can be used to set the dose.

In the particular embodiment discussed above, the transducer 30 is centered in the renal artery by the non-circular element 80 of expansible balloon 24. Other centering arrangements can be used. For example, an expansible balloon encompassing the transducer may be a balloon of circular cross-section slightly smaller in diameter than the renal artery 10. Such a balloon allows blood to continue to flow through the renal artery 10, but maintains the transducer 30 roughly centered in the renal artery 10. In this embodiment, the balloon 24 is dynamic rather than fitted to the renal artery 10 because the flow of blood around the balloon 24 causes small back and forth movements. This dynamic nature allows the blood to continue to reach all parts of the renal artery 10, thereby providing cooling and minimizing damage to the intima 3. In other embodiments, the distal and of the catheter can include expansible structures other than balloons, such as a wire basket or wire mesh structure which can be selectively brought to a radially expanded condition, such as by compressing the structure in the axial direction. The wire basket may be non-reflecting to ultrasound, or may be mounted on the catheter at a position axially offset from the transducer 30.

In a further variant, the balloon 24 may be formed from a porous membrane or include holes, such that cooled liquid being circulated within the balloon 24 may escape or be ejected from the balloon 24 into the blood stream within the renal artery 10. The escaping or ejected cooled liquid from the balloon 24 that enters the blood flow may support further cooling of the inner lining of the renal artery 10, which is in contact with the flowing blood.

Typically, catheter 18 is a disposable, single-use device. The catheter 18 or ultrasonic system 20 may contain a safety device that inhibits the reuse of the catheter 18 after a single use. Such safety devices per se are known in the art.

In yet another variant, the catheter 18 itself may include a steering mechanism which allows the physician to directly steer the distal end 22 of the catheter. The sheath may be omitted.

Another variation may be that an energy emitter unit at the distal end of the catheter 18, which includes the ultrasound transducer 30, may be positioned in the renal vein, and the ultrasound transducer 30 may include reflective or blocking structures for selectively directing ultrasound energy from the transducer 30 over only a limited range of radial directions to provide that ultrasound energy desirably is selectively directed from the transducer 30 in the renal vein toward the renal artery 10. When the venous approach is utilized, the ultrasound energy is directed into a segment or beam propagating away from an exterior surface of the transducer 30, commonly known as a side firing transducer 30 arrangement. For example, the ultrasound transducer 30 may have a construction and be operated to emit directed ultrasound energy 5 similarly as disclosed in US Provisional Application No. 61/256,002, filed Oct. 29, 2009, entitled "METHOD AND APPARATUS FOR PERCUTANEOUS TREATMENT OF MITRAL VALVE REGURGITATION (PMVR)," incorporated by reference herein. In this variation, the route by which the catheter 18 is introduced into the body, and then positioned close to the kidneys 6, is varied from the atrial approach discussed above. A venous approach may be utilized to take advantage of the potential for reduced closure issues after catheter 18 withdrawal.

Although the invention herein has been described with reference to particular embodiments, it is to be understood that these embodiments are merely illustrative of the principles and applications of the present invention. It is therefore to be understood that numerous modification may be made to the illustrative embodiments and that other arrangements may be devised without departing from the spirit and scope of the present invention as defined by the appended claims.

What is claimed is:

1. A system for inactivating renal nerve conduction in a mammalian subject having a renal artery, comprising:
    a catheter comprising a distal portion configured to be inserted into the renal artery of the mammalian subject;
    an ultrasound transducer positioned at the distal portion of the catheter, the ultrasound transducer configured to be inserted into the renal artery of the mammalian subject;
    an actuator electrically connected to the ultrasound transducer, the actuator configured to cause the ultrasound transducer to emit a dose of unfocused ultrasound energy into an impact volume of at least 0.5 cm$^3$;
    wherein the impact volume encompasses the renal artery so that the unfocused ultrasound energy is applied at a therapeutic level sufficient to inactivate conduction of renal nerves within the impact volume.

2. The system of claim 1, wherein the ultrasound transducer has a length between 2 mm and 10 mm and wherein the acoustic power output of the transducer is 10 to 100 Watts.

3. The system of claim 1, wherein:
    the ultrasound transducer has a length of 6 mm,
    the acoustic power output of the transducer is 10 to 100 Watts, and
    the duration of acoustic power application of the transducer is 10 seconds to 20 seconds.

4. The system of claim 1, wherein the ultrasound transducer is configured to emit the dose of unfocused ultrasound energy to inactivate conduction of the renal nerves along a length of 2 mm to 10 mm along an axis of the renal artery.

5. The system of claim 1, wherein the impact volume encompasses nerves adjacent to the renal artery.

6. The system of claim 1, wherein the ultrasound transducer is configured to emit the dose of unfocused ultrasound energy simultaneously in a 360° arc through an intima layer of the renal artery and into an adventitia layer of the renal artery.

7. The system of claim 1, wherein an optimal actuation frequency of the ultrasound transducer is approximately 9 MHz.

8. The system of claim 1, wherein:
    a balloon is mounted to the catheter to surround the ultrasound transducer, and
    the balloon is configured to engage a wall of the renal artery and, when inflated, to center the ultrasound transducer within the renal artery, the balloon further configured to receive a liquid delivered to the balloon to cool an intima layer of the renal artery.

9. The system of claim 1, further comprising a machine-readable element affixed to the catheter, the machine-readable element encoding an optimum actuation frequency of ultrasonic energy to be emitted by the ultrasound transducer during use.

10. The system of claim 7, wherein the ultrasound transducer is configured to emit the dose of unfocused ultrasound energy at a frequency sufficient to treat hypertension of the mammalian subject without causing stenosis of the renal artery.

11. The system of claim 1, wherein the ultrasound transducer is configured to emit the dose of unfocused ultrasound energy at a frequency of 8.5 to 9.5 MHz.

12. A method for inactivating renal nerve conduction along renal nerves associated with a renal artery in a mammalian subject, the method comprising:
    inserting an ultrasound transducer into a renal artery of the mammalian subject, wherein the ultrasound transducer is positioned along a distal portion of a catheter, the distal portion of the catheter comprising an expansible structure; and
    actuating the ultrasound transducer, using an actuator electrically connected to the ultrasound transducer, to cause emission of a dose of unfocused ultrasound energy into an impact volume of at least 0.5 cm$^3$;
    wherein the impact volume encompasses the renal artery so that the unfocused ultrasound energy is applied at a therapeutic level sufficient to inactivate conduction of renal nerves within the impact volume.

13. The method of claim 12, wherein the actuating the ultrasound transducer to cause emission of the dose of unfocused ultrasound energy is performed so as to maintain a temperature of the inner wall of the renal artery below 65° C. while heating the renal nerves in the impact volume to above 42° C.

14. The method of claim 12, further comprising:
    actuating the ultrasound transducer to emit unfocused ultrasound energy at a measurement level;

receiving an echo signal representing reflected measurement ultrasound energy;
measuring a time delay between the actuation of the ultrasound transducer and a return of the echo signal; and
determining the dose using a lookup table showing a relationship between the time delay and the dose.

15. The method of claim 12, further comprising:
actuating the ultrasound transducer to emit unfocused ultrasound energy at a measurement level;
receiving echo signals representing reflected measurement ultrasound energy;
measuring a time delay between the actuation of the ultrasound transducer and a return of the echo signals; and
determining the renal artery size based on the time delay.

16. The method of claim 12, further comprising:
actuating the ultrasound transducer to emit unfocused ultrasound energy at a measurement level;
receiving echo signals representing reflected measurement ultrasound energy;
measuring a range of time delays between the actuation of the ultrasound transducer and
the return of the echo signals indicating variation in the shape of the renal artery or that the transducer is off-center from the wall of the renal artery; and
adjusting the power of energy delivery based on the range of time delays.

17. The method of claim 12, further comprising:
actuating the ultrasound transducer to emit unfocused ultrasound energy at a measurement level toward the renal artery;
receiving echo signals representing reflected measurement ultrasound energy;
measuring a range of time delays between the actuation of the ultrasound transducer and the return of the echo signals indicating variation in the shape of the renal artery;
taking an average of the range of time delays to determine the average size of the renal artery; and
adjusting the power of energy delivery based on the average size of the renal artery.

18. The method of claim 12, further comprising:
transitioning the expansible balloon structure from a compressed state to a radially expanded state, wherein the expansible structure is a balloon;
inflating the balloon such that the balloon engages an inner wall of the renal artery and the ultrasound transducer is centered within the renal artery; and
delivering liquid to the balloon to cool an intima layer of the renal artery, wherein the actuating of the ultrasound transducer to inactivate conduction of the renal nerves does not cause damage to the intima layer of the renal artery.

19. The method of claim 12, wherein the ultrasound energy is transmitted at an acoustic power level of 10 to 100 Watts at a frequency of about 9 MHz for 10 seconds to 20 seconds, and wherein the dose of unfocused ultrasound energy is emitted in a pattern having a length of 2 mm to 10 mm along an axis of the renal artery.

20. The method of claim 12, further comprising:
using a reader to read an optimum actuation frequency of the transducer encoded on a machine-readable element specific to the transducer;
conveying the optimum actuation frequency of the transducer to a control board; and
using the control board to set a frequency for exciting the transducer.

21. The system of claim 8, wherein the balloon includes holes configured to permit the liquid to exit the balloon.

22. The system of claim 1, wherein the ultrasound transducer is of a tubular shape and has an exterior emitting surface in the form of a cylindrical surface of revolution about a proximal-to-distal axis of the transducer.

* * * * *